US007151139B2

(12) United States Patent
Tiller et al.

(10) Patent No.: US 7,151,139 B2
(45) Date of Patent: Dec. 19, 2006

(54) ANTIMICROBIAL POLYMERIC SURFACES

(75) Inventors: Joerg C. Tiller, Cambridge, MA (US); Chun-Jen Liao, Taipei (TW); Kim Lewis, Newton, MA (US); Alexander M. Klibanov, Newton, MA (US)

(73) Assignees: Massachusetts Institute of Technology, Cambridge, MA (US); Trustees of Tufts College, Medford, MA (US)

( * ) Notice: Subject to any disclaimer, the term of this patent is extended or adjusted under 35 U.S.C. 154(b) by 0 days.

(21) Appl. No.: 10/123,860

(22) Filed: Apr. 16, 2002

(65) Prior Publication Data

US 2003/0091641 A1 May 15, 2003

Related U.S. Application Data

(60) Provisional application No. 60/368,495, filed on Mar. 29, 2002, provisional application No. 60/340,078, filed on Dec. 10, 2001, provisional application No. 60/285,883, filed on Apr. 23, 2001.

(51) Int. Cl.
*C08L 67/02* (2006.01)

(52) U.S. Cl. .................... 525/165; 427/2.11; 427/2.12; 427/2.24; 427/2.25; 427/2.28; 428/448; 525/182; 525/186; 525/203; 525/421; 525/445

(58) Field of Classification Search ............... 427/2.11, 427/2.12, 2.24, 2.25, 2.28; 428/448; 525/165, 525/182, 186, 203, 421, 445
See application file for complete search history.

(56) References Cited

U.S. PATENT DOCUMENTS

| | | | | |
|---|---|---|---|---|
| 3,868,340 A | | 2/1975 | Keegan et al. | 260/17.4 |
| 4,327,073 A | * | 4/1982 | Huang | 436/44 |
| 4,404,196 A | | 9/1983 | Daudt et al. | 424/184 |
| 4,460,747 A | | 7/1984 | Horak et al. | 525/197 |
| 4,511,677 A | * | 4/1985 | Horton et al. | 521/28 |
| 4,542,125 A | | 9/1985 | Gorman et al. | 514/57 |
| 4,847,088 A | | 7/1989 | Blank | 424/404 |
| 4,866,192 A | | 9/1989 | Plueddemann et al. | 556/410 |
| 4,867,898 A | | 9/1989 | Spaulding et al. | 252/143 |
| 4,888,434 A | | 12/1989 | Sawaragi et al. | 556/418 |
| 4,898,957 A | | 2/1990 | Pleueddemann et al. | 556/418 |
| 4,921,701 A | | 5/1990 | Blehm Blank | 424/401 |
| 4,933,327 A | | 6/1990 | Plueddemann et al. | 514/63 |
| 4,985,023 A | | 1/1991 | Blank et al. | 604/360 |
| 4,990,338 A | | 2/1991 | Blank et al. | 424/443 |
| 5,035,892 A | | 7/1991 | Blank et al. | 424/443 |
| 5,045,322 A | | 9/1991 | Blank et al. | 424/486 |
| 5,061,487 A | | 10/1991 | Blank et al. | 424/81 |
| 5,064,613 A | | 11/1991 | Higgs et al. | 422/16 |
| 5,073,298 A | | 12/1991 | Gentle et al. | 252/358 |
| 5,079,004 A | | 1/1992 | Blank et al. | 424/404 |
| 5,100,689 A | | 3/1992 | Goldberg et al. | 427/2 |
| 5,112,903 A | | 5/1992 | Sakakibara et al. | 525/54.2 |
| 5,126,138 A | | 6/1992 | McGee et al. | 424/404 |
| 5,145,596 A | | 9/1992 | Blank et al. | 252/106 |
| 5,169,561 A | | 12/1992 | Gentle et al. | 252/321 |
| 5,169,625 A | | 12/1992 | Blank | 424/65 |
| 5,216,176 A | | 6/1993 | Heindel et al. | 459/280 |
| 5,244,667 A | | 9/1993 | Hagiwara et al. | 424/409 |
| 5,356,929 A | | 10/1994 | Heindel et al. | 514/455 |
| 5,359,104 A | | 10/1994 | Higgs et al. | 556/406 |
| 5,473,083 A | | 12/1995 | Heindel et al. | 549/280 |
| 5,520,664 A | | 5/1996 | Bricault, Jr. et al. | 604/265 |
| 5,573,797 A | | 11/1996 | Wilhoit | 426/106 |
| 5,573,800 A | | 11/1996 | Wilhoit | 426/326 |
| 5,573,801 A | | 11/1996 | Wilhoit | 426/326 |
| 5,578,598 A | | 11/1996 | Abe et al. | 514/255 |
| 5,656,611 A | | 8/1997 | Kabanov et al. | 514/44 |
| 5,716,709 A | | 2/1998 | Ferguson et al. | 428/420 |
| 5,861,149 A | | 1/1999 | Ritter | 424/78.06 |
| 6,013,615 A | | 1/2000 | Zhou et al. | 510/434 |
| 6,022,553 A | | 2/2000 | Anders et al. | 424/411 |
| 6,033,719 A | | 3/2000 | Keogh | 427/212 |
| 6,086,863 A | | 7/2000 | Ritter et al. | 424/78.06 |
| 6,284,723 B1 | | 9/2001 | Zhou et al. | 510/384 |
| 2002/0068092 A1 | | 6/2002 | Bosch et al. | 424/501 |

FOREIGN PATENT DOCUMENTS

| | | |
|---|---|---|
| EP | 0 275 015 B1 | 7/1988 |
| WO | WO 99/20105 | 4/1999 |
| WO | WO 00/69264 | 11/2000 |
| WO | WO 01/07090 A1 | 2/2001 |

OTHER PUBLICATIONS

"Hawley's Condensed Chemical Dictionary", 12th ed., Lewis, Sr., ed., Van Nostrand Reinhold Co., New York, pp. 21-22, 35 (1993).*
Park, et al., "Bacterial Adhesion On PEG Modified Polyurethane Surfaces", Biomaterials 19, pp. 851-859 (1998).
Tiller, et al., "Designing Surfaces That Kill Bacteria On Contact", PNAS, vol. 98, No. 11, pp. 5981-5985 (2001).
Supplementary European Search Report.

* cited by examiner

*Primary Examiner*—Peter D. Mulcahy
(74) *Attorney, Agent, or Firm*—Pabst Patent Group LLP

(57) ABSTRACT

Bactericidal compositions are disclosed that comprise a polymeric compound immobilized on a material. Medical devices are also disclosed which comprise such a bactericidal composition. Methods are disclosed for covalently derivatizing the surfaces of common materials with an antibacterial polycation, e.g., poly(vinyl-N-pyridinium bromide); the first step of the methods involves coating the surface with a nanolayer of silica. Various commercial synthetic polymers derivatized in this manner are bactericidal, i.e., they kill on contact up to 99% of deposited Gram-positive and Gram-negative bacteria, whether deposited through air or water.

20 Claims, 9 Drawing Sheets

ANTIMICROBIAL POLYMERIC SURFACES

RELATED APPLICATIONS

This application claims the benefit of priority to U.S. Provisional Patent Application Ser. No. 60/285,883, filed Apr. 23, 2001; U.S. Provisional Patent Application Ser. No. 60/340,078, filed Dec. 10, 2001; and U.S. Provisional Patent Application Ser. No. 60/368,495, filed Mar. 29, 2002.

GOVERNMENT SUPPORT

This invention was made with support provided by the National Institutes of Health (Grant No. GM26698) and the National Science Foundation (Grant No. DMR-9400334); therefore, the government has certain rights in this invention.

BACKGROUND OF THE INVENTION

Due to the ever-growing demand for healthy living, there is a keen interest in materials capable of killing harmful microorganisms. Such materials could be used to coat surfaces of common objects touched by people in everyday lives, e.g., door knobs, children toys, computer keyboards, telephones, etc., to render them antiseptic and thus unable to transmit bacterial infections. Since ordinary materials are not antimicrobial, their modification is required. For example, surfaces chemically modified with poly(ethylene glycol) and certain other synthetic polymers can repel (although not kill) microorganisms (Bridgett, M. J., et al, S. P. (1992) *Biomaterials* 13, 411–416. Arciola, C. R., et al Alvergna, P., Cenni, E. & Pizzoferrato, A. (1993) *Biomaterials* 14, 1161–1164. Park, K. D., Kim, Y. S., Han, D. K., Kim, Y. H., Lee, E. H. B., Suh, H. & Choi, K. S. (1998) *Biomaterials* 19, 851–859.)

Alternatively, materials can be impregnated with antimicrobial agents, such as antibiotics, quarternary ammonium compounds, silver ions, or iodine, that are gradually released into the surrounding solution over time and kill microorganisms there (Medlin, J. (1997) *Environ. Health Persp.* 105, 290–292; Nohr, R. S. & Macdonald, G. J. (1994) *J. Biomater. Sci., Polymer Edn.* 5, 607–619 Shearer, A. E. H., et al (2000) *Biotechnol. Bioeng.* 67, 141–146.). Although these strategies have been verified in aqueous solutions containing bacteria, they would not be expected to be effective against airborne bacteria in the absence of a liquid medium; this is especially true for release-based materials, which are also liable to become impotent when the leaching antibacterial agent is exhausted.

Infection is a frequent complication of many invasive surgical, therapeutic and diagnostic procedures. For procedures involving implantable medical devices, avoiding infection can be particularly problematic because bacteria can develop into biofilms, which protect the microbes from clearing by the subject's immune system. As these infections are difficult to treat with antibiotics, removal of the device is often necessitated, which is traumatic to the patient and increases the medical cost.

Any material left embedded in the body provides a surface for accumulation of infectious microorganisms, particularly bacteria and occasionally fungi. This is understood to take place through the formation of biofilms. A biofilm is a type of fouling that occurs when microorganisms attach to surfaces and secrete a hydrated polymeric matrix that surrounds them. Microorganisms existing in a biofilm, termed sessile, grow in a protected environment that insulates them from attack from antimicrobial agents. These sessile communities can give rise to nonsessile individuals, termed planktonic, which rapidly multiply and disperse. These planktonic organisms are responsible for invasive and disseminated infections. They are the targets of antimicrobial therapy. Conventional treatments fail to eradicate the sessile communities rooted in the biofilm. Biofilms are understood to be a frequently occurring reservoir for infectious agents. The biology of biofilms is described in more detail in "Bacterial biofilms: a common cause of persistent infection," J. Costerson, P. Stewart, E. Greenberg, Science 284: 1318–1322 (1999), and "The riddle of biofilm resistance," K. Lewis, Antimicrob. Agents Chemother., 45, 999–1007 (2001), incorporated herein by reference.

Biofilms develop preferentially on inert surfaces or on non-living tissue, and occur commonly on medical devices and devascularized or dead tissues. Biofilms have been identified on sequestra of dead bone and on bone grafts, from which they can incite an invasive infection called osteomyelitis that can kill even more bone. Biofilms have been also identified on living, hypovascular tissues such as native heart valves, where they are responsible for the devastating infection called endocarditis where the microorganism not only can colonize distant locations by seeding throughout the bloodstream, but also can destroy the heart valve itself. Infections involving implanted medical devices generally involve biofilms, where a sessile community provides a reservoir for an invasive infection. The presence of microorganisms in a biofilm on a medical device represents contamination of that foreign body. The elicitation by the biofilm of clinically perceptible host responses constitutes an infection.

The development of an infection from an area of contamination is consistent with the natural history of biofilm growth and development. Biofilms grow slowly, in one or more locations, colonized by one or a plurality of microorganisms. The pattern of biofilm development involves initial attachment of a microorganism to a solid surface, the formation of microcolonies attached to the surface, and finally the differentiation of the microcolonies into exopolysaccharide-encased mature biofilms. Planktonic cells are released from biofilms in a natural pattern of programmed detachment, so that the biofilm serves as a nidus for multiple, recurrent acute invasive infections. Antibiotics typically treat the infection caused by the planktonic organisms, but fail to kill those sessile organisms protected in the biofilm.

Sessile microorganisms also give rise to localized symptoms, releasing antigens and stimulating antibody production that activates the immune system to attack the biofilm and the area surrounding it. Antibodies and host immune defenses are ineffective in killing the organisms in the biofilm, even though these organisms have elicited the antibody and related immune response. The cytotoxic products of the host's immunologically activated cells can be directed towards the host's own tissues. This phenomenon is seen in the mouth, where the host's response to the dental biofilm can inflame tissues surrounding the teeth and give rise to periodontitis. This phenomenon can also give rise to local inflammation around implanted medical devices and bone resorption with loosening of orthopedic and dental implants.

While host defenses may hold invasive infections in check by controlling the proliferation of planktonic organisms, this favorable equilibrium presupposes an intact immune system. Many patients in a hospital setting have compromised immune systems, rendering them more vulnerable to invasive infections once a biofilm community has become established. Patients requiring implantable medical devices may likewise have compromised immune systems, whether on a short-term or long-term basis. A poorly functioning immune system puts the host at greater risk for initial formation of a contaminated biofilm around a medical device and for the invasion of planktonic organisms into the surrounding tissues and the system. Once the planktonic organisms mount a full-scale infection, the immunocompromised host will be less likely to contain and control it, with potentially lethal results.

Protected from antibiotic treatment and host defenses, the microorganisms in a biofilm typically cause recurrent infections and low-grade local symptoms. The biofilm, once established, can only be eradicated surgically. When a foreign object becomes contaminated with microorganisms, the only way to eliminate local and systemic infection may be to remove the contaminated foreign article. If the material being removed is essential for health, a similar article may need to be replaced in the same location; the replacement article will be especially prone to infection because of the residual microorganisms in the area.

Since the difficulties associated with eliminating biofilm-based infections are well-recognized, a number of technologies have developed to treat surfaces or fluids bathing surfaces to prevent or impair biofilm formation. Biofilms adversely affect medical systems and other systems essential to public health such as water supplies and food production facilities. A number of technologies have been proposed that treat surfaces with organic or inorganic materials to interfere with biofilm development. For example, various methods have been employed to coat the surfaces of medical devices with antibiotics (See e.g. U.S. Pat. Nos. 4,107,121, 4,442,133, 4,895,566, 4,917,686, 5,013,306, 4,952,419, 5,853,745 and 5,902,283) and other bacteriostatic compounds (See e.g U.S. Pat. Nos. 4,605,564, 4,886,505, 5,019,096, 5,295,979, 5,328,954, 5,681,575, 5,753,251, 5,770,255, and 5,877,243). Despite these technologies, contamination of medical devices and invasive infection therefrom continues to be a problem.

Infectious organisms are ubiquitous in the medical environment, despite vigorous efforts to maintain antisepsis. The presence of these organisms can result in infection of hospitalized patients and medical personnel. These infections, termed nosocomial, often involve organisms more virulent and more unusual than those encountered outside the hospital. In addition, hospital-acquired infections are more likely to involve organisms that have developed resistance to a number of antibiotics. Although cleansing and anti-bacterial regimens are routinely employed, infectious organisms readily colonize a variety of surfaces in the medical environment, especially those surfaces exposed to moisture or immersed in fluid. Even barrier materials, such as gloves, aprons and shields, can spread infection to the wearer or to others in the medical environment. Despite sterilization and cleansing, a variety of metallic and non-metallic materials in the medical environment can retain dangerous organisms trapped in a biofilm, thence to be passed on to other hosts.

Any agent used to impair biofilm formation in the medical environment must be safe to the user. Certain biocidal agents, in quantities sufficient to interfere with biofilms, also can damage host tissues. Antibiotics introduced into local tissue areas can induce the formation of resistant organisms which can then form biofilm communities whose planktonic microorganisms would likewise be resistant to the particular antibiotics. Any anti-biofilm or antifouling agent must furthermore not interfere with the salubrious characteristics of a medical device. Certain materials are selected to have a particular type of operator manipulability, softness, water-tightness, tensile strength or compressive durability, characteristics that cannot be altered by an agent added for anti-microbial effects.

As a further problem, it is possible that materials added to the surfaces of implantable devices to inhibit contamination and biofilm formation may be thrombogenic. Some implantable materials are of themselves thrombogenic. For example, it has been shown that contact with metal, glass, plastic or other similar surfaces can induce blood to clot. Heparin compounds, which are known to have anticoagulant effects, have therefore been applied to certain medical devices prior to implantation. However, there are few known products in the medical arsenal whose antimicrobial effects are combined with antithrombogenic effects. This combination would be particularly valuable to treat those medical devices that reside in the bloodstream, such as heart valves, artificial pumping devices ("artificial hearts" or left ventricular assist devices), vascular grafting prostheses and vascular stents. In these settings, clot formation can obstruct the flow of blood through the conduit and can furthermore break off pieces called emboli that are carried downstream, potentially blocking circulation to distant tissues or organs.

Biofilm formation has important public health implications. Drinking water systems are known to harbor biofilms, even though these environments often contain disinfectants. Any system providing an interface between a surface and a fluid has the potential for biofilm development. Water cooling towers for air conditioners are well-known to pose public health risks from biofilm formation, as episodic outbreaks of infections like Legionnaires' Disease attest. Turbulent fluid flow over the surface does not provide protection: biofilms can form in conduits where flowing water or other fluids pass, with the effects of altering flow characteristics and passing planktonic organisms downstream. Industrial fluid processing operations have experienced mechanical blockages, impedance of heat transfer processes, and biodeterioration of fluid-based industrial products, all attributable to biofilms. Biofilms have been identified in flow conduits like hemodialysis tubing, and in water distribution conduits. Biofilms have also been identified to cause biofouling in selected municipal water storage tanks, private wells and drip irrigation systems, unaffected by treatments with up to 200 ppm chlorine.

Biofilms are a constant problem in food processing environments. Food processing involves fluids, solid material and their combination. As an example, milk processing facilities provide fluid conduits and areas of fluid residence on surfaces. Cleansing milking and milk processing equipment presently utilizes interactions of mechanical, thermal and chemical processes in an air-injected clean-in-place methods. Additionally, the milk product itself is treated with pasteurization. In cheese producing, biofilms can lead to the production of calcium lactate crystals in Cheddar cheese. Meat processing and packing facilities are in like manner susceptible to biofilm formation. Non-metallic and metallic surfaces can be affected. Biofilms in meat processing facilities have been detected on rubber "fingers," plastic curtains, conveyor belt material, evisceration equipment and stainless steel surfaces. Controlling biofilms and microorganism contamination in food processing is hampered by the additional need that the agent used not affect the taste, texture or aesthetics of the product.

There exists, therefore, a need to be able to render general surfaces bactericidal. General surface coating/derivatization procedures have been developed that should be applicable to most materials regardless of their nature.

SUMMARY OF THE INVENTION

One aspect of the present invention is directed to antimicrobial surfaces comprised of covalently attached amphipathic compounds. In certain embodiments, a surface of the present invention acts to eliminate airborne biologics on contact. In certain embodiments, a surface of the present invention acts to eliminate waterborne biologics on contact. In certain embodiments, a surface of the present invention acts to prevent the formation of biofilms.

In certain embodiments, said covalently attached amphipathic compound is a polymer comprising ammonium ions. In a preferred embodiment, said polymer has a molecular weight of at least 10,000 g/mol, more preferably 120,000 g/mol, and most preferably 150,000 g/mol.

In certain embodiments, the surface of the present invention is glass. In certain other embodiments, the surface of the present invention is a plastic. In a particular embodiment, the surface of the present invention is an amino-bearing glass.

In certain embodiments, the present invention relates to a composition, comprised of a material and a compound immobilized at said material, wherein said immobilized compound is a polymer, wherein said polymer is not insoluble in water. In certain embodiments, said immobilized compound is a polycation. In certain embodiments, said immobilized compound is a water-soluble lipophilic polycation. In certain embodiments, said immobilized compound is covalently linked to said solid material. In certain embodiments, said immobilized compound comprises poly (N-alkyl vinylpyridine) or poly(N-alkyl ethylene imine).

In certain embodiments, the compound covalently bonded to the surface is represented by the formula I:

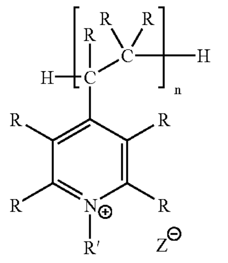

I wherein

R represents individually for each occurrence hydrogen, alkyl, alkenyl, alkynyl, acyl, aryl, carboxylate, alkoxycarbonyl, aryloxycarbonyl, carboxamido, alkylamino, acylamino, alkoxyl, acyloxy, hydroxyalkyl, alkoxyalkyl, aminoalkyl, (alkylamino)alkyl, thio, alkylthio, thioalkyl, (alkylthio)alkyl, carbamoyl, urea, thiourea, sulfonyl, sulfonate, sulfonamido, sulfonylamino, or sulfonyloxy;

R' represents independently for each occurrence alkyl, an alkylidene tether to a surface, or an acyl tether to a surface;

Z represents independently for each occurrence Cl, Br, or I; and n is an integer less than or equal to about 1500.

In a preferred embodiment, the invention comprises Poly (4-vinyl-N-alkylpyridinium bromide) or poly(methacryloyloxydodecylpyridinium bromide) (MDPB) covalently attached to a glass surface. In another preferred embodiment, the invention comprises an N-alkylated poly(4-vinyl pyridine) covalently attached to a glass surface.

In certain embodiments, the biologics killed on the surfaces of the instant invention are bacteria. In a particular embodiment, the bacteria killed are Gram-positive bacteria. In another particular embodiment, the bacteria killed are Gram-negative bacteria.

In certain embodiments, the invention is drawn to a method for rendering a surface bactericidal. In certain embodiments, the surface to be rendered bactericidal comprises amino functionality. In certain embodiments the method for rendering a surface bactericidal comprises derivatizing a surface possessing amino functionality to form a covalently bound polymer comprising quaternary amine groups on said surface.

In certain embodiments, the surface to be rendered bactericidal does not have amino functionality, but amino functionality is added to said surface by applying a layer of $SiO_2$ nanoparticles to said surface which form Si—OH groups upon hydration, and which are then treated with an amination agent to form a surface comprising amino functionality. In certain embodiments, the amination agent is 3-aminopropyltriethoxysilane.

In certain embodiments the invention is drawn to a bacteria resistant article comprising a covalently bound polymer upon its surface wherein the covalently bound polymer comprises quaternary ammonium groups. In certain embodiments the bacteria resistant article is a household item. In certain embodiments the bacteria resistant article is a medical device.

DETAILED DESCRIPTION OF THE INVENTION

A. Overview

Figure 1:
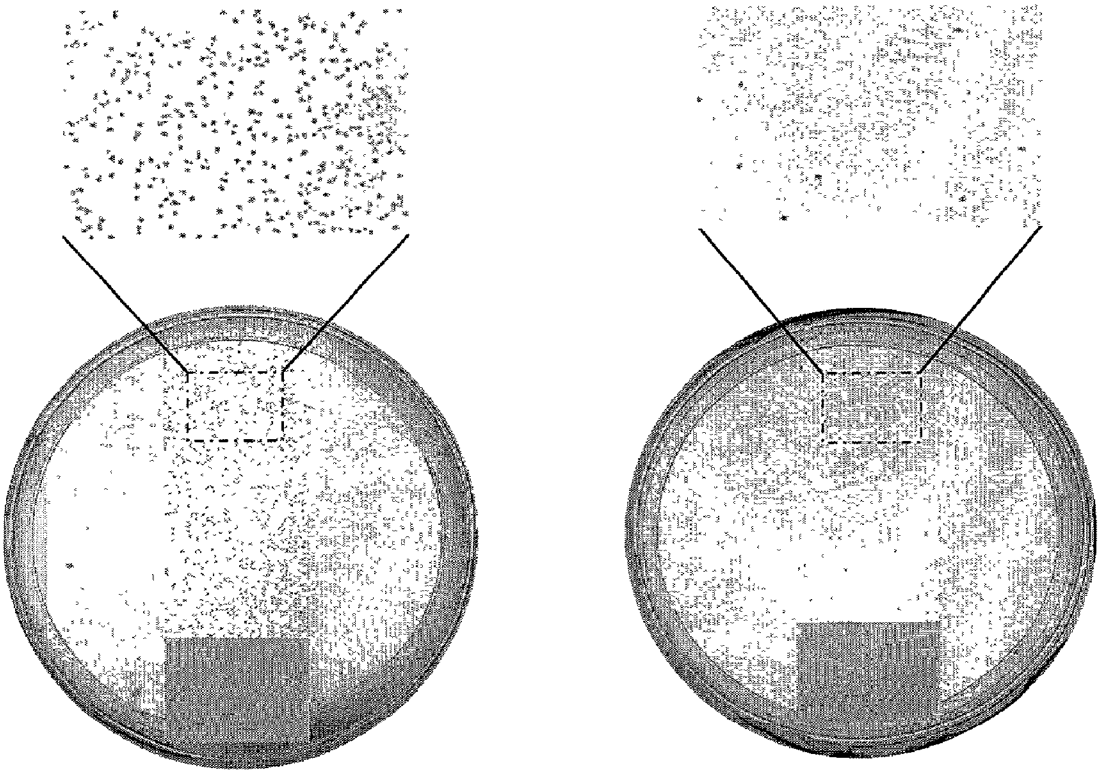
FIG. 1 depicts a commercial $NH_2$-glass slide (left) and a hexyl-PVP- modified slide (right) onto which aqueous suspensions (approximately $10^6$ cells/mL of distilled water) of *S. aureus* cells were sprayed, air dried for 2 min, and incubated under 0.7% agar in a bacterial growth medium at 37° C. overnight.

In general, the present invention relates to the prevention of accumulation of microorganisms on any surface wherein such accumulation has a deleterious effect on human or animal health. In particular, the present invention relates to the prevention of those conditions affecting human or animal health that involve fouling. Fouling events involve recognition between a biologic and a surface, adhesion of the biologic to the surface, and the subsequent activity of the biologic. As understood herein, the formation of a biofilm is a type of fouling. Biofilms with health effects commonly contain infectious microorganisms.

In a health-related environment, fouling can result in biofilm formation. Biofilm formation is understood to cause local contamination of an affected area with potential for invasive local infection and for systemic infection. Microorganisms may damage tissues in at least three ways: 1) they can enter or contact host cells and directly cause cell death; 2) they can release endotoxins or exotoxins that kill cells at a distance, release enzymes that degrade tissue components, or damage blood vessels and cause ischemic necrosis; and 3) they can induce host-cellular responses that, although directed against the invader, may cause additional tissue damage, including suppuration, scarring and hypersensitivity reactions. An infection, whether local or systemic, represents the penetration of microorganisms into a host with the production of tissue damage or the elicitation of host defense mechanisms or both, leading to clinically identifiable symptoms. Common local symptoms can include pain, tenderness, swelling and interference with function. Common systemic symptoms can include fever, malaise and hyperdynamic cardiovascular effects. Massive bloodstream invasion by infectious agents can rapidly become fatal.

When an infection has its origins in a biofilm surrounding an object in the body, whether a naturally occurring object or a foreign one, the infection often cannot be controlled without removing that object. If the object is naturally occurring, like devascularized or necrotic tissue, it is removed surgically via a process called debridement. If the object is a foreign one, such as a medical device, it is removed entirely. At times a rim of tissue must be removed along with the contaminated object to ensure maximal removal of contaminating material. If the material being removed is essential for health, a similar article may need to be replaced in the same location; the replacement article will be especially prone to infection because of the residual microorganisms in the area.

The present invention is directed to antimicrobial surfaces comprised of amphipathic compounds that can covalently attached to a surface. In certain embodiments, this surface acts to eliminate airborne biologics on contact, such as bacteria. In a preferred embodiment, the compound is an amphipathic polycation.

B. Definitions

For convenience, certain terms employed in the specification, examples, and appended claims are collected here.

The term "biologic" as used herein refers to any bacterium, fungus, virus, protozoan, parasite, or other infective agent capable of causing disease in humans or non-human animals.

"Contacting" as used herein refers to any means for providing the compounds of the invention to a surface to be protected from biofouling. Contacting can include spraying, wetting, immersing, dipping, painting, bonding or adhering or otherwise providing a surface with a compound of the invention.

A "coating" refers to any temporary, semipermanent or permanent layer, covering or surface. A coating can be a gas, vapor, liquid, paste, semi-solid or solid. In addition a coating can be applied as a liquid and solidify into a hard coating. Examples of coatings include polishes, surface cleaners, caulks, adhesives, finishes, paints, waxes polymerizable compositions (including phenolic resins, silicone polymers, chlorinated rubbers, coal tar and epoxy combinations, epoxy resin, polyamide resins, vinyl resins, elastomers, acrylate polymers, fluoropolymers, polyesters and polyurethanes, latex). Silicone resins, silicone polymers (e.g. RTV polymers) and silicone heat cured rubbers are suitable coatings for use in the invention and described for example in the Encyclopedia of Polymer Science and Engineering (1989) 15: 204 et seq. Coatings can be ablative or dissolvable, so that the dissolution rate of the matrix controls the rate at which AF agents are delivered to the surface. Coatings can also be non-ablative, and rely on diffusion principles to deliver an AF agent to the surface. Non-ablative coatings can be porous or non-porous. A coating containing an AF agent freely dispersed in a polymer binder is referred to as "monolithic" coating. Elasticity can be engineered into coatings to accommodate pliability, e.g. swelling or shrinkage, of the surface to be coated.

A "component" is a part of an apparatus that is structurally integrated with that apparatus. A component may be applied to a surface of an apparatus, contained within the substance of the apparatus, retained in the interior of the apparatus, or any other arrangement whereby that part is an integral element of the structure of the apparatus. As an example, the silicone covering surrounding the mechanical part of a pacemaker is a component of the pacemaker. A component may be the lumen of an apparatus where the lumen performs some function essential to the overall function of the apparatus. The lumen of a tissue expander port is a component of the tissue expander. A component can refer to a reservoir or a discrete area within the apparatus specifically adapted for the delivery of a fluid to a surface of the apparatus. A reservoir within an implantable drug delivery device is a component of that device.

A "delivery system" refers to any system or apparatus or component whereby the disclosed antifouling compounds can be delivered to a surface upon which biofilm formation is to be inhibited. Representative delivery systems can include encapsulation of the agent, incorporation of the agent in the substance of an article of manufacture, or inserting the agent into the matrices or pores of a suitable object, so that the agent is able to reach the targeted surface in sufficient amount to inhibit biofilm. A delivery system can comprise a coating. A delivery system can comprise a mechanical object adapted for the delivery of the antifouling compound to a surface. Other mechanisms comprising delivery systems will be apparent to those of skill in the relevant arts.

"Dressing" refer to any bandage or covering applied to a lesion or otherwise used to prevent or treat infection. Examples include wound dressings for chronic wounds (such as pressure sores, venous stasis ulcers and burns) or acute wounds and dressings over percutaneous devices such as IVs or subclavian lines intended to decrease the risk of line sepsis due to microbial invasion. For example, the compositions of the invention could be applied at the percutaneous puncture site, or could be incorporated in the adherent dressing material applied directly over the entry site.

The phrase "effective amount" refers to an amount of the disclosed antifouling compounds that significantly reduces the number of organisms that attach to a defined surface (cells/$mm^2$) relative to the number that attach to an untreated surface. Particularly preferred are amounts that reduce the number of organisms that attach to the surface by a factor of at least 2. Even more preferred are amounts that reduce the surface attachment of organisms by a factor of 4, more preferably by a factor of 6. An effective amount of the disclosed antifouling compound is said to inhibit the formation of biofilms, and to inhibit the growth of organisms on a defined surface. The term "inhibit," as applied to the effect of an antifouling compound on a surface includes any action that significantly reduces the number of organisms that attach thereto.

The term "health-related environment" is understood to include all those environments where activities are carried out that are implicated in the restoration or maintenance of human health. A health-related environment can be a medical environment, where activities are carried out directly or indirectly intended to restore human health. An operating room, a doctor's office, a hospital room, and a factory making medical equipment are all examples of medical environments. Other health-related environments can include industrial or residential sites where activities pertaining to human health are carried out. Such activities include food processing, water purification, and sanitation.

An "implant" is any object intended for placement in a human body that is not a living tissue. Implants include naturally derived objects that have been processed so that their living tissues have been devitalized. As an example, bone grafts can be processed so that their living cells are removed, but so that their shape is retained to serve as a template for ingrowth of bone from a host. As another example, naturally occurring coral can be processed to yield hydroxyapatite preparations that can be applied to the body for certain orthopedic and dental therapies. An implant can also be an article comprising artificial components. The term "implant" can be applied to the entire spectrum of medical devices intended for placement in a human body.

The terms "infectious microorganisms" or "infectious agents" as used herein refers to disease causing or contributing bacteria (including Gram-negative and Gram-positive organisms, such as *Staphylococci* sps. (e.g. *Staphylococcus aureus, Staphylococcus epidermis*), *Enterococcus* sp. (*E. faecalis*), *Pseudomonas* sp. (*P. aeruginosa*), *Escherichia* sp. (*E. coli*), *Proteus* sp. (*P. mirabilis*)), fungi (including *Candida albicans*), viruses and protists.

"Medical device" refers to a non-naturally occurring object that is inserted or implanted in a subject or applied to a surface of a subject. Medical devices can be made of a variety of biocompatible materials, including: metals, ceramics, polymers, gels and fluids not normally found within the human body. Examples of polymers useful in fabricating medical devices include such polymers as silicones, rubbers, latex, plastics, polyanhydrides, polyesters, polyorthoesters, polyamides, polyacrylonitrile, polyurethanes, polyethylene, polytetrafluoroethylene, polyethylenetetraphthalate and polyphazenes. Medical devices can also be fabricated using certain naturally-occurring materials or treated naturally-occurring materials. As an example, a heart valve can be fabricated by combining a treated porcine heart valve with an affixation apparatus using artificial materials. Medical devices can include any combination of artificial materials, combinations selected because of the particular characteristics of the components. For example, a hip implant can include a combination of a metallic shaft to bear the weight, a ceramic artificial joint and a polymeric glue to affix the structure to the surrounding bone. An implantable device is one intended to be completely imbedded in the body without any structure left outside the body (e.g. heart valve). An insertable device is one that is partially imbedded in the body but has a part intended to be external (e.g. a catheter or a drain). Medical devices can be intended for short-term or long-term residence where they are positioned. A hip implant is intended for several decades of use, for example. By contrast, a tissue expander may only be needed for a few months, and is removed thereafter. Insertable devices tend to remain in place for shorter times than implantable devices, in part because they come into more contact with microorganisms that can colonize them.

The term "soluble" refers to the ability to be loosened or dissolved.

The term "surface" or "surfaces" can mean any surface of any material, including glass, plastics, metals, polymers, and like. It can include surfaces constructed out of more than one material, including coated surfaces.

Biofilm formation with health implications can involve those surfaces in all health-related environments, including surfaces found in medical environments and those surfaces in industrial or residential environments that are involved in those functions essential to well-being like nutrition, sanitation and the prevention of disease.

A surface of an article adapted for use in a medical environment can be capable of sterilization using autoclaving, biocide exposure, irradiation or gassing techniques like ethylene oxide exposure. Surfaces found in medical environments include the inner and outer aspects of various instruments and devices, whether disposable or intended for repeated uses. Examples include the entire spectrum of articles adapted for medical use, including scalpels, needles, scissors and other devices used in invasive surgical, therapeutic or diagnostic procedures; implantable medical devices, including artificial blood vessels, catheters and other devices for the removal or delivery of fluids to patients, artificial hearts, artificial kidneys, orthopedic pins, plates and implants; catheters and other tubes (including urological and biliary tubes, endotracheal tubes, peripherably insertable central venous catheters, dialysis catheters, long term tunneled central venous catheters, peripheral venous catheters, short term central venous catheters, arterial catheters, pulmonary catheters, Swan-Ganz catheters, urinary catheters, peritoneal catheters), urinary devices (including long term urinary devices, tissue bonding urinary devices, artificial urinary sphincters, urinary dilators), shunts (including ventricular or arterio-venous shunts); prostheses (including breast implants, penile prostheses, vascular grafting prostheses, heart valves, artificial joints, artificial larynxes, otological implants), vascular catheter ports, wound drain tubes, hydrocephalus shunts, pacemakers and implantable defibrillators, and the like. Other examples will be readily apparent to practitioners in these arts.

Surfaces found in the medical environment include also the inner and outer aspects of pieces of medical equipment, medical gear worn or carried by personnel in the health care setting. Such surfaces can include counter tops and fixtures in areas used for medical procedures or for preparing medical apparatus, tubes and canisters used in respiratory treatments, including the administration of oxygen, of solubilized drugs in nebulizers and of anesthetic agents. Also included are those surfaces intended as biological barriers to infectious organisms in medical settings, such as gloves, aprons and faceshields. Commonly used materials for biological barriers may be latex-based or non-latex based. Vinyl is commonly used as a material for non-latex surgical gloves. Other such surfaces can include handles and cables for medical or dental equipment not intended to be sterile. Additionally, such surfaces can include those non-sterile external surfaces of tubes and other apparatus found in areas where blood or body fluids or other hazardous biomaterials are commonly encountered.

Surfaces in contact with liquids are particularly prone to biofilm formation. As an example, those reservoirs and tubes used for delivering humidified oxygen to patients can bear biofilms inhabited by infectious agents. Dental unit waterlines similarly can bear biofilms on their surfaces, providing a reservoir for continuing contamination of the system of flowing and aerosolized water used in dentistry.

Sprays, aerosols and nebulizers are highly effective in disseminating biofilm fragments to a potential host or to another environmental site. It is understood to be especially important to health to prevent biofilm formation on those surfaces from whence biofilm fragments can be carried away by sprays, aerosols or nebulizers contacting the surface.

Other surfaces related to health include the inner and outer aspects of those articles involved in water purification, water storage and water delivery, and those articles involved in food processing. Surfaces related to health can also include the inner and outer aspects of those household articles involved in providing for nutrition, sanitation or disease prevention. Examples can include food processing equipment for home use, materials for infant care, tampons and toilet bowls.

The term 'Gram-positive bacteria' is an art recognized term for bacteria characterized by having as part of their cell wall structure peptidoglycan as well as polysaccharides and/or teichoic acids and are characterized by their blue-violet color reaction in the Gram-staining procedure. Representative Gram-positive bacteria include: *Actinomyces* spp., *Bacillus anthracis, Bifidobacterium* spp., *Clostridium botulinum, Clostridium perfringens, Clostridium* spp., *Clostridium tetani, Corynebacterium diphtheriae, Corynebacterium jeikeium, Enterococcus faecalis, Enterococcus faecium, Erysipelothrix rhusiopathiae, Eubacterium* spp., *Gardnerella vaginalis, Gemella morbillorum, Leuconostoc* spp., *Mycobacterium abcessus, Mycobacterium avium* complex, *Mycobacterium chelonae, Mycobacterium fortuitum, Mycobacterium haemophilium, Mycobacterium kansasii, Mycobacterium leprae, Mycobacterium marinum, Mycobacterium scrofulaceum, Mycobacterium smegmatis, Mycobacterium terrae, Mycobacterium tuberculosis, Mycobacterium ulcerans, Nocardia* spp., *Peptococcus niger, Peptostreptococcus* spp., *Proprionibacterium* spp., *Staphylococcus aureus, Staphylococcus auricularis, Staphylococcus capitis, Staphylococcus cohnii, Staphylococcus epidermidis, Staphylococcus haemolyticus, Staphylococcus hominis, Staphylococcus lugdanensis, Staphylococcus saccharolyticus, Staphylococcus saprophyticus, Staphylococcus schleiferi, Staphylococcus similans, Staphylococcus warneri, Staphylococcus xylosus, Streptococcus agalactiae* (group B streptococcus), *Streptococcus anginosus, Streptococcus bovis, Streptococcus canis, Streptococcus equi, Streptococcus milleri, Streptococcus mitior, Streptococcus mutans, Streptococcus pneumoniae, Streptococcus pyogenes* (group A streptococcus), *Streptococcus salivarius, Streptococcus sanguis.*

The term "Gram-negative bacteria" is an art recognized term for bacteria characterized by the presence of a double membrane surrounding each bacterial cell. Representative Gram-negative bacteria include *Acinetobacter calcoaceticus, Actinobacillus actinomycetemcomitans, Aeromonas hydrophila, Alcaligenes xylosoxidans,* Bacteroides, *Bacteroides fragilis, Bartonella bacilliformis, Bordetella* spp., *Borrelia burgdorferi, Branhamella catarrhalis, Brucella* spp., *Campylobacter* spp., *Chalmydia pneumoniae, Chlamydia psittaci, Chlamydia trachomatis, Chromobacterium violaceum, Citrobacter* spp., *Eikenella corrodens, Enterobacter aerogenes, Escherichia coli, Flavobacterium meningosepticum, Fusobacterium* spp., *Haemophilus influenzae, Haemophilus* spp., *Helicobacter pylori, Klebsiella* spp., *Legionella* spp., *Leptospira* spp., *Moraxella catarrhalis, Morganella morganii, Mycoplasma pneumoniae, Neisseria gonorrhoeae, Neisseria meningitidis, Pasteurella multocida, Plesiomonas shigelloides, Prevotella* spp., *Proteus* spp., *Providencia rettgeri, Pseudomonas aeruginosa, Pseudomonas* spp., *Rickettsia prowazekii, Rickettsia rickettsii, Rochalimaea* spp., *Salmonella* spp., *Salmonella typhi, Serratia marcescens, Shigella* spp., *Treponema carateum, Treponema pallidum, Treponema pallidum endemicum, Treponema pertenue, Veillonella* spp., *Vibrio cholerae, Vibrio vulnificus, Yersinia enterocolitica, Yersinia pestis.*

An amphipathic molecule or compound is an art recognized term where one end of the molecule or compound is polar and another end is non-polar.

The term "polar" is art-recognized. A polar compound contains substances with asymmetric charge distribution. In general, a non-polar substance will dissolve non-polar molecules, and a polar substance will dissolve polar molecules, e.g. water, a polar substance, dissolves other polar substances. An amphipathic compound has a portion which is soluble in aqueous solvents, and a portion which is insoluble aqueous solvents.

The term "ligand" refers to a compound that binds at the receptor site.

The term "heteroatom" as used herein means an atom of any element other than carbon or hydrogen. Preferred heteroatoms are boron, nitrogen, oxygen, phosphorus, sulfur and selenium.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma ($\sigma$) constant. This well known constant is described in many references, for instance, J. March, *Advanced Organic Chemistry,* McGraw Hill Book Company, New York, (1977 edition) pp. 251–259. The Hammett constant values are generally negative for electron donating groups (σ[P]=−0.66 for $NH_2$) and positive for electron withdrawing groups (σ[P]=0.78 for a nitro group), (σ[P] indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 3–10 carbon atoms in their ring structure, and more preferably have 5, 6 or 7 carbons in the ring structure.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, $—CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, $—CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, $—CF_3$, —CN, or the like.

The term "carbocycle", as used herein, refers to an aromatic or non-aromatic ring in which each atom of the ring is carbon.

As used herein, the term "nitro" means $—NO_2$; the term "halogen" designates —F, —Cl, —Br or —I; the term "sulfhydryl" means —SH; the term "hydroxyl" means —OH; and the term "sulfonyl" means $—SO_2—$.

The terms "amine" and "amino" are art-recognized and refer to both unsubstituted and substituted amines, e.g., a moiety that can be represented by the general formula:

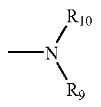

or

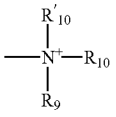

wherein $R_9$, $R_{10}$ and $R'_{10}$ each independently represent a group permitted by the rules of valence.

The term "acylamino" is art-recognized and refers to a moiety that can be represented by the general formula:

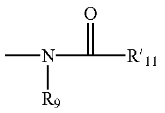

wherein $R_9$ is as defined above, and $R'_{11}$ represents a hydrogen, an alkyl, an alkenyl or $—(CH_2)_m—R_8$, where m and $R_8$ are as defined above.

The term "amido" is art recognized as an amino-substituted carbonyl and includes a moiety that can be represented by the general formula:

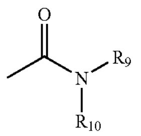

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are defined above. Representative alkylthio groups include methylthio, ethyl thio, and the like.

The term "carbonyl" is art recognized and includes such moieties as can be represented by the general formula:

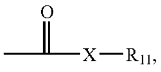

or

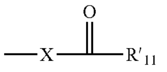

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O-$(CH_2)_m$—$R_8$, where m and $R_8$ are described above.

The term "sulfonate" is art recognized and includes a moiety that can be represented by the general formula:

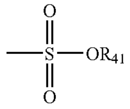

in which $R_{41}$ is an electron pair, hydrogen, alkyl, cycloalkyl, or aryl.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry;* this list is typically presented in a table entitled *Standard List of Abbreviations.* The abbreviations contained in said list, and all abbreviations utilized by organic chemists of ordinary skill in the art are hereby incorporated by reference.

The term "sulfate" is art recognized and includes a moiety that can be represented by the general formula:

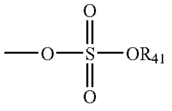

in which $R_{41}$ is as defined above.

The term "sulfonylamino" is art recognized and includes a moiety that can be represented by the general formula:

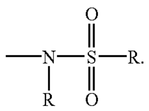

The term "sulfamoyl" is art-recognized and includes a moiety that can be represented by the general formula:

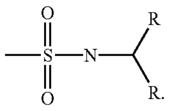

The term "sulfonyl", as used herein, refers to a moiety that can be represented by the general formula:

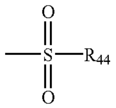

in which $R_{44}$ is selected from the group consisting of hydrogen, alkyl, alkenyl, alkynyl, cycloalkyl, heterocyclyl, aryl, or heteroaryl.

The term "sulfoxido" as used herein, refers to a moiety that can be represented by the general formula:

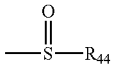

in which $R_{44}$ is selected from the group consisting of hydrogen, alkyl, alkenyl, alkynyl, cycloalkyl, heterocyclyl, aralkyl, or aryl.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g. alkyl, m, n, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis,* 2nd ed.; Wiley: New York, 1991).

Contemplated equivalents of the compounds described above include compounds which otherwise correspond thereto, and which have the same general properties thereof (e.g., functioning as analgesics), wherein one or more simple variations of substituents are made which do not adversely affect the efficacy of the compound in binding to opioid receptors. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986–87, inside cover.

C. Compounds

One aspect of the present invention is directed to antimicrobial surfaces comprised of covalently attached amphipathic compounds. In certain embodiments, a surface of the present invention acts to eliminate airborne biologics on contact. In certain embodiments, a surface of the present invention acts to eliminate waterborne biologics on contact. In certain embodiments, a surface of the present invention acts to prevent the formation of biofilms.

In certain embodiments, said covalently attached amphipathic compound is a polymer comprising ammonium ions. In a preferred embodiment, said polymer has a molecular weight of at least 10,000 g/mol, more preferably 120,000 g/mol, and most preferably 150,000 g/mol.

In certain embodiments, the surface of the present invention is glass. In certain other embodiments, the surface of the present invention is a plastic. In a particular embodiment, the surface of the present invention is an amino-bearing glass.

In certain embodiments, the compound covalently bonded to the surface is represented by the formula I:

I

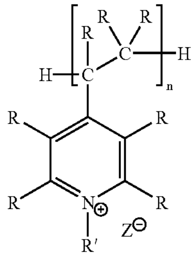

wherein

R represents individually for each occurrence hydrogen, alkyl, alkenyl, alkynyl, acyl, aryl, carboxylate, alkoxycarbonyl, aryloxycarbonyl, carboxamido, alkylamino, acylamino, alkoxyl, acyloxy, hydroxyalkyl, alkoxyalkyl, aminoalkyl, (alkylamino)alkyl, thio, alkylthio, thioalkyl, (alkylthio)alkyl, carbamoyl, urea, thiourea, sulfonyl, sulfonate, sulfonamido, sulfonylamino, or sulfonyloxy;

R' represents independently for each occurrence alkyl, an alkylidene tether to a surface, or an acyl tether to a surface;

Z represents independently for each occurrence Cl, Br, or I; and n is an integer less than or equal to about 1500.

In a preferred embodiment, the invention comprises Poly(4-vinyl-N-alkylpyridinium bromide) or poly(methacryloyloxydodecylpyridinium bromide) (MDPB) covalently attached to a glass surface. In another preferred embodiment, the invention comprises an N-alkylated poly(4-vinyl pyridine) covalently attached to a glass surface.

In certain embodiments, the biologics killed on the surfaces of the instant invention are bacteria. In a particular embodiment, the bacteria killed are Gram-positive bacteria. In another particular embodiment, the bacteria killed are Gram-negative bacteria.

Modification of Surface Containing Reactive Amino Groups

In one embodiment, the surface is modified by graft copolymerization. In this case (Method A), the surface is prepared by acylating a $NH_2$-glass slide with an acylating agent to introduce double bonds. In particular embodiment, the acylating agent is acryloyl chloride. This is followed by copolymerization with a copolymerizing agent, for example, 4-vinylpyridine. A immobilized polymer, such as polyvinylpyridine, PVP, was found to afford approximately the same number of viable *S. aureus* cells after spraying the bacterial suspension onto its surface as a plain $NH_2$-glass slide.

The final step in creating the surface is to introduce positive charges into the polymer chains attached to glass. For example, the PVP pyridine rings may be N-alkylated by seven linear alkyl bromides (with chain lengths varying from propyl to hexadecyl). This procedure is exemplified in Example 1. This method tends to produce mostly linearly attached, straight chain polymers to the surface.

Figure 2:
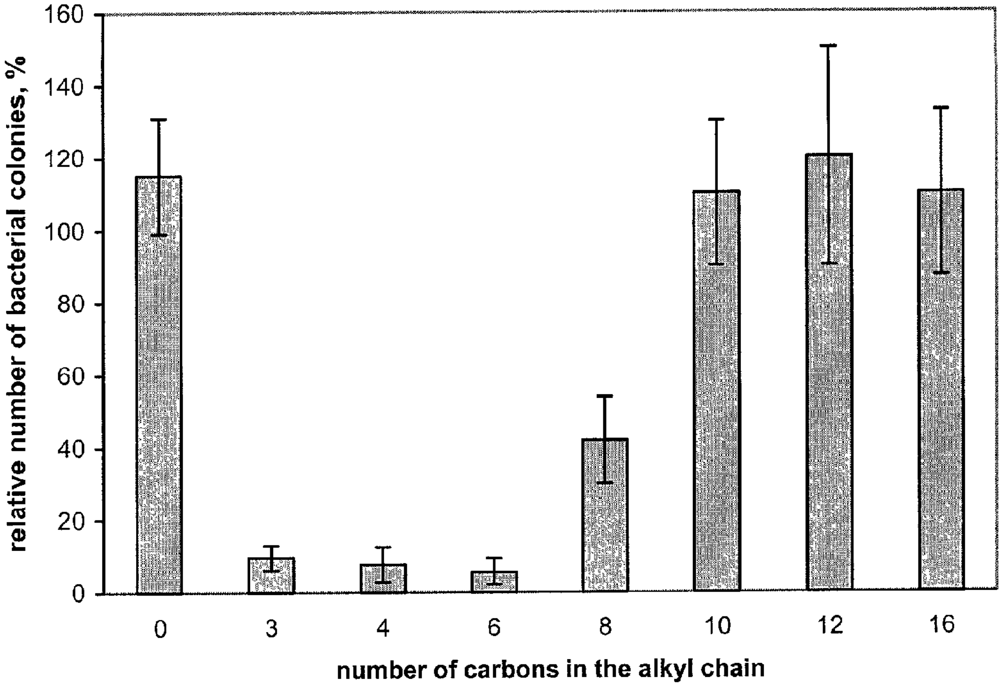
FIG. 2 depicts the percentage of *S. aureus* colonies grown on the infected surfaces of glass slides modified with PVP N-alkylated with different linear alkyl bromides relative to the number of colonies grown on a commercial $NH_2$-glass slide.
Figure 3:
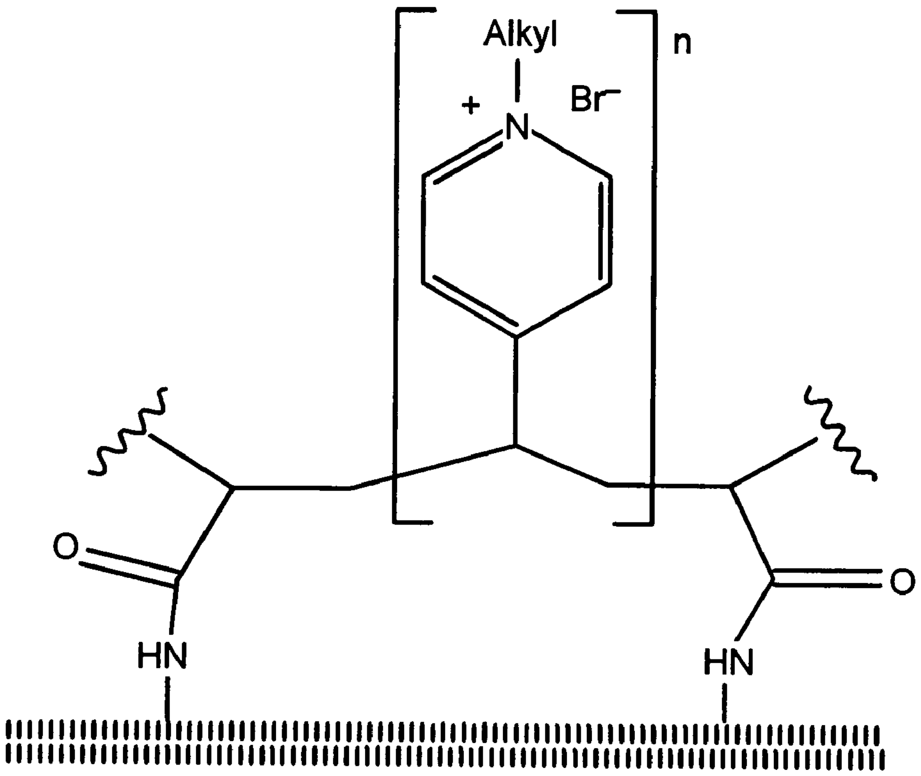
FIG. 3 depicts a compound of the present invention prepared by Method A.

The resultant slide surfaces were examined with respect to their ability to kill on contact *S. aureus* cells sprayed on them. As seen in FIG. 2, propylated, butylated, hexylated, and octylated immobilized PVP chains were effective in markedly reducing the number of viable bacterial cells, with the most effective, hexyl-PVP affording a 94±4% reduction (right portion of FIG. 1). In contrast, the immobilized PVP N-alkylated by decyl through hexadecyl bromides, as well as the non-alkylated chains, were totally ineffective (FIG. 2).

This behavior pattern may correlate with the visual appearance of the alkylated PVP-slides. While non-alkylated, decyl-, dodecyl-, and hexadecyl-PVP-modified slides were all cloudy (absorbance at 400 nm, $A_{400}$, of some 0.1), an octyl-PVP-modified slide was much less so ($A_{400}$=0.03), and propyl-, butyl-, and hexyl-PVP-modified slides were clear ($A_{400}$<0.002). The cloudiness reflects polymer aggregates formed on the surface, with such aggregates apparently being unable to interact with bacterial cells. The non-alkylated immobilized PVP chains, as well as those modified with long alkyl moieties, may stick to each other due to hydrophobic interactions; in contrast, in immobilized PVP chains modified with short alkyl groups, such interactions are not strong enough to overcome the electrostatic repulsion of the positively charged polymers.

Using hexyl-PVP (henceforth referred to as that prepared by method A), the bactericidal effect of this surface toward another Gram-positive bacterium, *S. epidermidis,* as well as two Gram-negative bacteria, *E. coli* and *P. aeruginosa* is investigated. The first two formed colonies of the same size as *S. aureus* (FIG. 1, left portion) when sprayed on $NH_2$-glass slides, whereas the colonies of *P. aeruginosa* were larger but still distinguishable. As seen in Table 1 (method A), the number of colonies all three bacteria formed after spraying onto hexyl-PVP-slides dropped more than 100-fold compared to the plain $NH_2$-glass.

TABLE 1

The ability of hexyl-PVP attached to glass slides by two different methods to kill various airborne bacteria on contact.

| | | Percentage of bacteria killed | |
|---|---|---|---|
| Bacterium | Gram | Method A | Method B |
| *S. aureus* | (+) | 94 ± 4 | 94 ± 3 |
| *S. epidermidis* | (+) | >99 | >99 |
| *P. aeruginosa* | (−) | >99.8 | >99.8 |
| *E. coli* | (−) | >99 | >99 |

In another embodiment, the surface is prepared by alkylation of the surface using halogenated alkyl groups. These reactive alkyl groups are then used for attachment of the polymer. The polymer chains were then further alkylated to increase the positive charge. This method yields mostly branched and looped polymers covalently bonded to the surface.

For example, a $NH_2$-glass slide was alkylated with 1,4-dibromobutane to introduce reactive bromobutyl groups which were subsequently used for the attachment of PVP. To increase the positive charge of the attached PVP chains, the chains were further N-alkylated with hexyl bromide (found optimal in method A, see FIG. 2). After *S. aureus* cells were sprayed, air dried, and cultured, the resultant hexyl-PVP-slides (henceforth referred to as those prepared by method B) looked essentially the same as shown in the right portion of FIG. 1. Compared to a $NH_2$-glass slide, 94±3% of the deposited *S. aureus* cells were killed (the last column, 1st line, of Table 1).

The molecular weight of the immobilized polymer was found to be important for the antibacterial properties of the surface. For example a hexyl-PVP-slide prepared using method B with shorter PVP chains, 60,000 instead of 160,000 g/mol, killed only 62±8% of the deposited *S. aureus* cells.

Inspection of the remainder of the data in Table 1 reveals that method B afforded the slide surface which was as deadly toward *S. epidermidis, P. aeruginosa,* and *E. coli* as that obtained via method A.

Previously described materials that kill bacteria by releasing bactericidal agents are eventually depleted of the active substance due to its release into the surrounding solution. To test whether the antibacterial polymers immobilized using our methodology can leach from the glass surface, hexyl-PVP-slides prepared via methods A and B were placed into polystyrene petri dishes, and aqueous suspensions of *S. aureus* cells were sprayed on them as well as on the non-antibacterial polystyrene. After air drying and incubation under growth agar, it was observed that only a few (some 3 per $cm^2$) colonies were growing on both types of the hexyl-PVP-glass slides, while a far larger number of colonies (60±10 per $cm^2$) was growing on the surrounding petri dishes, even in the immediate proximity of the slides. The lack of inhibition zones around the hexyl-PVP slides, typical of the release of bactericidal agents (23), indicates that the immobilized bactericidal polymer hexyl-PVP does not leach from the slides, i.e., that the bacteria are indeed killed on contact with the slide's surface.

To test how unique the ability to kill airborne bacteria is among dry surfaces, an *S. aureus* cell suspension was sprayed on various common materials, including metals, synthetic and natural polymers, and ceramics. The number of colonies remaining viable in all instances was compared to that on $NH_2$-glass. As seen in Table 2, none of the materials examined significantly lowered the amount of bacterial cells remaining viable after spraying.

TABLE 2

The number of *S. aureus* cells remaining viable after their aqueous suspensions have been sprayed onto various materials.

| Material | Relative numbers of viable bacterial cells % |
|---|---|
| plain glass | 83 ± 10 |
| polystyrene | 105 ± 15 |
| polypropylene | 97 ± 9 |
| aluminum | 72 ± 7 |
| steel | 95 ± 15 |
| paper | 77 ± 8 |
| wood (birch) | 102 ± 10 |
| porcelain | 85 ± 10 |
| PVP slide | 115 ± 16 |
| HPVP slide (method A) | 6 ± 4 |
| HPVP slide (method B) | 6 ± 3 |

Modification of Surface that does not Contain Active Amino Groups

Since it would be desirable to make numerous diverse objects bactericidal, a surface derivatization approach potentially applicable to any material was developed. Ordinary commercial synthetic polymers, namely polyolefins, a polyamide, and a polyester, which by themselves exhibit no antibacterial activity, were used to test the approach. A slide made of high-density polyethylene (HDPE) was selected as the initial target. This polymer, as many other materials, lacks reactive groups suitable for a facile chemical modification. Therefore, we decided to coat it with an ultrathin silica layer by a combustion chemical vapor deposition technique. Schinkinger, B., Petzold, R., Tiller, H.-J. & Grundmeier, G. Chemical structure and morphology of ultrathin combustion CVD layers on zinc coated steel. *Appl. Surf. Sci.* 179, 79–87 (2001). To this end, we employed (step #1 in FIG. 4) a pen-like torch containing a compressed mixture of 0.6% tetramethylsilane with 7:3 propane-butane (Pyrosil®). When this mixture burns in the air, tetramethylsilane is oxidized to form 2–5-nm $SiO_2$ nanoparticles which cover a surface to which the flame is applied. Tiller, H. J., Goebel, R., Magnus, B., Garschke, A. & Musil, R. A new concept of metal-resin adhesion using an intermediate layer of silicon oxide ($SiO_x$)-carbon. *Thin Solid Films* 169, 159–168 (1989). The resulting dense, ~100-nm thick $SiO_2$ layer chemically resembling glass (polysiloxane), can thereafter be readily chemically modified in a uniform fashion regardless of the nature of the bulk material. Schinkinger, B., Petzold, R., Tiller, H.-J. & Grundmeier, G. Chemical structure and morphology of ultrathin combustion CVD layers on zinc coated steel. *Appl. Surf. Sci.* 179, 79–87 (2001). Tiller, H. J., Goebel, R., Magnus, B., Garschke, A. & Musil, R. A new concept of metal-resin adhesion using an intermediate layer of silicon oxide ($SiO_x$)-carbon. *Thin Solid Films* 169, 159–168 (1989). Tiller, H. J., Kaiser, W. D., Kleinert, H. & Goebel, R. The Silicoater method improves bond strength and resistance to aging. *Adhaesion* 33, 27–31 (1989). Tiller, H. J., Goebel, R. & Gutmann, N. Silicate coupling layer for metal to polymer adhesion improvement. Physical-chemical fundamentals and technological importance. *Makromol. Chem., Macromol. Symp.* 50, 125–135 (1991).

The visual appearance of the HDPE surface did not change after the $SiO_2$ coating procedure. The degree of crosslinking of such a $SiO_2$ layer is lower than that of glass, and numerous Si—OH groups are formed on hydration by water adsorbed from the environment after the deposition process. Schinkinger, B., Petzold, R., Tiller, H.-J. & Grundmeier, G. Chemical structure and morphology of ultrathin combustion CVD layers on zinc coated steel. *Appl. Surf. Sci.* 179, 79–87 (2001). Because of these Si—OH groups, the coated HDPE surface is expected to be hydrophilic, in contrast to the very hydrophobic unmodified polymer. To quantify this difference, we measured the contact angle formed by an aqueous drop on a surface, a common method of determining the water affinity of materials. David, J. The idea of water repellency. *Text. Inst. Ind.* 4, 293–5 (1966). To this end, 0.1 mL of distilled water was placed on the HDPE surface. The angle between the core of the resultant water drop and the surface under it was estimated to be some 120°, indicative of a hydrophobic material. When the same amount of distilled water was placed onto the $SiO_2$-coated HDPE, the water spread on the surface and the contact angle was less than 10° reflecting the surface's hydrophilic character. Independently, the presence of the $SiO_2$ layer on the HDPE slide was confirmed by the silicon and oxygen signals detected in the X-ray photoelectron spectrum.

Next, amino groups were introduced into the $SiO_2$-coated HDPE slide surface by reacting it with 3-aminopropyltriethoxysilane (step #2 in FIG. 4), a standard procedure for the amination of glass surfaces. Bisse, E., Scholer, A. & Vonderschmitt, D. J. A new method for coupling glucose dehydrogenase to glass tubes activated with titanium tetrachloride. *FEBS Lett.* 138, 316–318 (1982). The $NH_2$-functionalized HDPE slide was subsequently alkylated with 1,4-dibromobutane to introduce bromoalkyl groups (step #3 in FIG. 4), which were then reacted with PVP in presence of 1-bromohexane (step #4 in FIG. 4). Under the conditions used, only a few pyridine groups of the PVP chain (approximately 1,500 pyridine groups per chain) are alkylated by the surface-bound bromoalkyls, with the majority being alkylated by 1-bromohexane. Tiller, J. C., Liao, C.-J., Lewis, K. & Klibanov, A. M. Designing surfaces that kill bacteria on contact. *Proc. Natl. Acad. Sci. U.S.A.* 98, 5981–5985 (2001). The number of the pyridinium groups on the resultant hexyl-PVP-derivatized polyethylene slides, titrated spectrophotometrically with fluorescein, was determined to be 8.2±1.9 nmol/$cm^2$, which is similar to that observed for hexyl-PVP-modified $NH_2$-glass. Tiller, J. C., Liao, C.-J., Lewis, K. & Klibanov, A. M. Designing surfaces that kill bacteria on contact. *Proc. Natl. Acad. Sci. U.S.A.* 98, 5981–5985 (2001).

Figure 4:
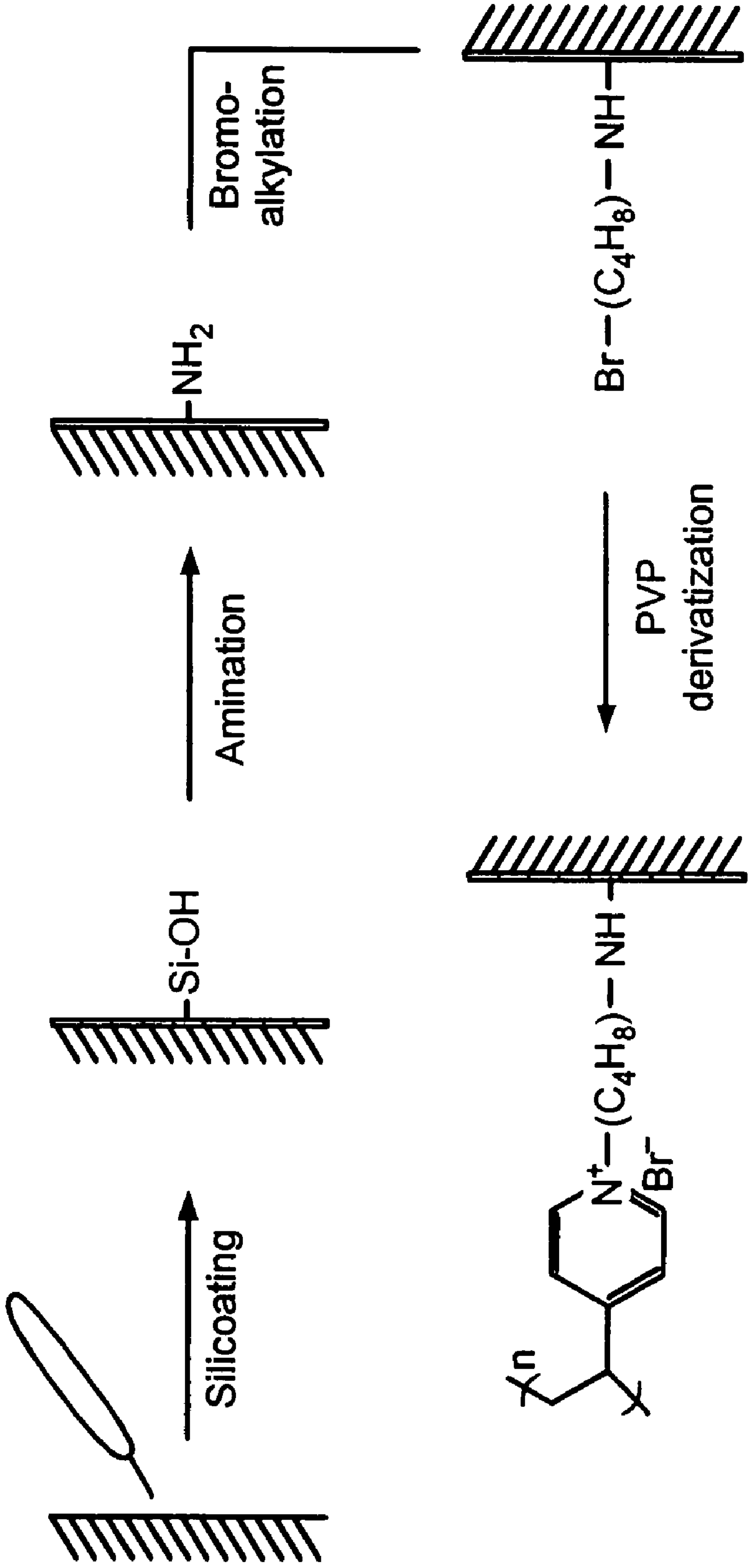
FIG. 4 depicts a schematic illustration of the derivatization of polymer surfaces with poly(vinyl-N-hexylpyridinium bromide) (hexyl-PVP), comprising the following four steps: coating with a $SiO_2$ nanolayer using the combustion chemical vapor deposition; treating with 3-aminopropyltriethoxysilane; alkylating with 1,4-dibromobutane; and derivatizing with hexyl-PVP in the presence of 1-bromohexane.

The generality of the foregoing coating/derivatization approach was confirmed by modifying two other industrial polyolefins, low-density polyethylene (LDPE) and polypropylene (PP), as well as the polyamide nylon and the polyester poly(ethylene terephthalate) (PET). All these synthetic polymers were successfully derivatized as shown in FIG. 4 and exhibited surface densities of the pyridinium groups similar to that of HDPE—8.5±1.8 (LDPE), 7.2±2.1 (PP), 8.0±1.1 (nylon), and 7.5±0.9 (PET) nmol/$cm^2$. All hexyl-PVP-derivatized slides, starting with HDPE, were subsequently examined with respect to their ability to kill airborne bacteria on contact.

Figure 5:
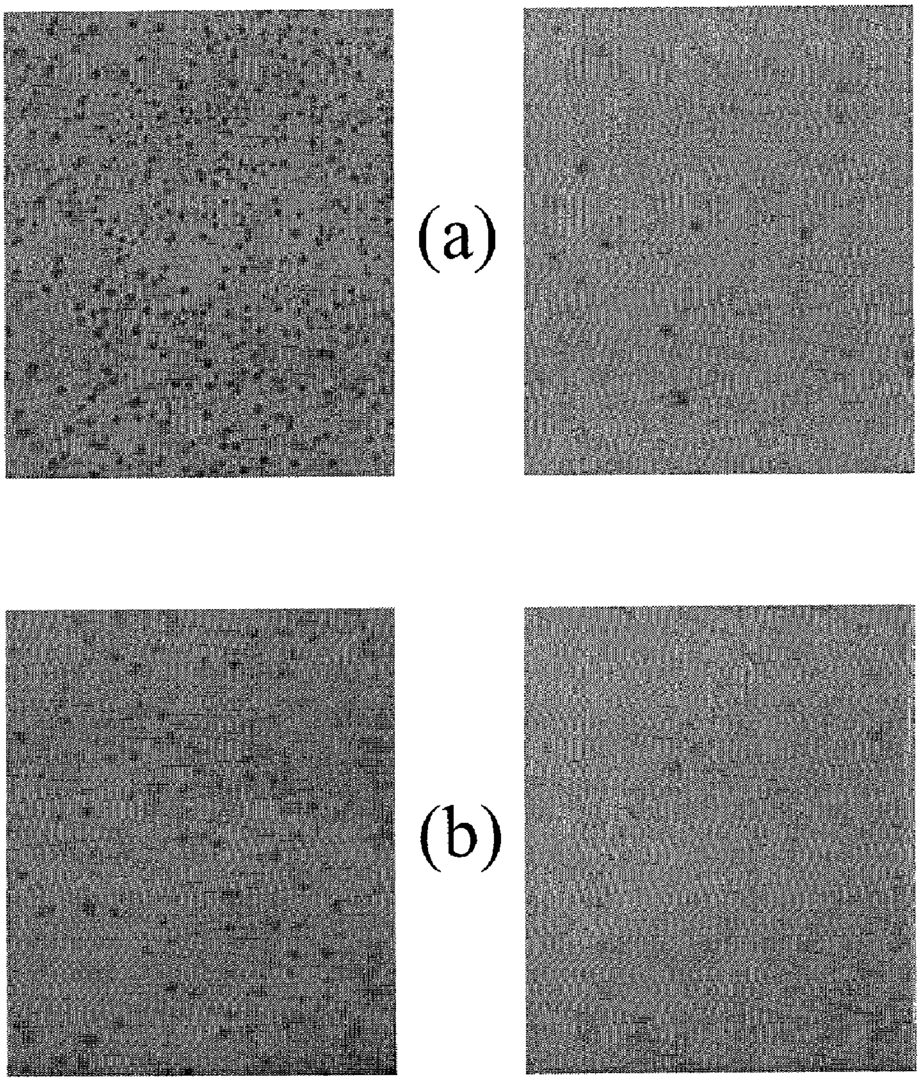
FIG. 5 depicts photographs of a commercial HDPE slide (left) and the hexyl-PVP-derivatized slide (right) onto which aqueous suspensions (approximately $10^6$ cells/mL of distilled water) of (a) *S. aureus* or (b) *E. coli* cells were sprayed, followed by air drying for 2 min and incubation under 0.7% agar in a bacterial growth medium at 37° C. overnight.

To simulate natural deposition of airborne bacteria, a suspension in distilled water of the ubiquitous pathogen Gram-positive bacterium *Staphylococcus aureus* was sprayed onto a slide surface and the latter was allowed to dry. Xiong, Y., Yeaman, M. R. & Bayer, A. S. Linezolid: A new antibiotic. *Drugs Today* 36, 529–539 (2000). The slide was then incubated under nutrient agar overnight as described earlier, and the number of viable bacterial cells was determined by colony count. Tiller, J. C., Liao, C.-J., Lewis, K. & Klibanov, A. M. Designing surfaces that kill bacteria on contact. *Proc. Natl. Acad. Sci. U.S.A.* 98, 5981–5985 (2001). As seen in FIG. 5*a*, left, numerous readily distinguishable bacterial colonies grew on the unmodified HDPE slide. The number of colonies grown on the $SiO_2$-coated or $NH_2$-functionalized HDPE slides (FIG. 4) was essentially the same indicating that these modifications are not toxic to *S. aureus*. In sharp contrast, when sprayed onto a hexyl-PVP-modified HDPE slide, 96±3% of the deposited bacterial cells became non-viable (FIG. 5*a*, right, and Table 3).

TABLE 3

The ability of various commercial synthetic polymers derivatized by hexyl-PVP to kill airborne bacteria on contact.

| | | Percentage of bacteria killed | | | | |
|---|---|---|---|---|---|---|
| Bacterium | Type | HDPE | LDPE | PP | nylon | PET |
| *S. aureus* | Gram (+) | 96 ± 3 | 97 ± 1 | 90 ± 3 | 92 ± 2 | 95 ± 1 |
| *E. coli* | Gram (−) | 97 ± 1 | 96 ± 2 | 98 ± 1 | 98 ± 2 | 95 ± 1 |

Suspensions of bacteria ($10^6$ cells/mL for *S. aureus* and $10^5$ cells/mL for *E. coli*) in distilled water were sprayed on a hexyl-PVP-modified polymer slide, and the latter was air dried for 2 min and incubated under 0.7% agar in a bacterial growth medium overnight; thereafter, the colonies were counted. The number of viable cells obtained in the same manner with the corresponding unmodified polymer slides was used as a standard (i.e., 0% of the bacteria killed). Abbreviations for the polymer materials used are as follows: LDPE—low-density polyethylene, HDPE—high-density polyethylene, PP—polypropylene, and PET—poly(ethylene terephthalate). All experiments were performed at least in duplicate, and the errors given indicate the standard deviations.

LDPE, PP, nylon, and PET derivatized with hexyl-PVP were analogously tested for their ability to kill airborne *S. aureus*. As seen in Table 3, in all cases the number of bacterial colonies formed plunged 10 to 30-fold compared to those grown on the corresponding unmodified slides.

Next, we tested the killing efficiency of the hexyl-PVP-derivatized surfaces for a representative Gram-negative bacterium, *Escherichia coli*. As seen in FIG. 5*b*, left, many *E. coli* colonies grown on a HDPE slide after spraying, while less dense than those of *S. aureus* grown under the same conditions, are still distinguishable. The surface derivatization with hexyl-PVP slashed their number by 97±3% (FIG. 5*b*, right, and Table 3). Inspection of the remaining data in the last line of Table 3 reveals that the hexyl-PVP modification of LDPE, PP, nylon, and PET slides likewise afforded a 20 to 50-fold drop in the viable *E. coli* cells, following their deposition from the airborne state, when compared to the corresponding unmodified slides.

To test whether the hexyl-PVP chains immobilized using our methodology can leach from the slide surface (and possibly only then kill the deposited bacteria), modified HDPE slide was placed into a polystyrene Petri dish, and an aqueous suspension of *S. aureus* cells was sprayed on it, as well as on the (non-antibacterial) polystyrene surface. After air drying and incubation under growth agar, only a few (4±2 per $cm^2$) colonies grew on the hexyl-PVP-modified HDPE slide, while a far greater number of colonies (85±5 per cm2) grew on the surface of the surrounding Petri dish, even in the immediate proximity of the slide. The lack of inhibition zones around the hexyl-PVP-slides, characteristic of a release of bactericidal agents, indicates that the immobilized polycation does not leach from the slide, i.e., that the airborne bacteria are indeed killed on contact with the slide's surface. Kawabata, N. & Nishiguchi, M. Antibacterial activity of soluble pyridinium-type polymers. *Appl. Environ. Microbiol* 54, 2532–2535 (1988).

Another important question was whether the hexyl-PVP-derivatized slides can also kill waterborne bacteria. To experimentally simulate a flowing aqueous solution, a polymer slide was placed vertically in a bacterial suspension in PBS, pH 7.0, and the resulting system was gently agitated at 37° C. After a 2-h incubation, the slide was washed with the sterile buffer to remove non-adhered bacteria and then incubated in sterile PBS under the conditions outlined above for 1 h to allow the tentatively adhered bacteria to either detach or adhere irreversibly. Wiencek, K. M. & Fletcher, M. Bacterial adhesion to hydroxyl- and methyl-terminated alkanethiol self-assembled monolayers. *J Bacteriol.* 177, 1959–1966 (1995). After rinsing the slide with PBS, it was immediately covered with a layer of solid growth agar and incubated overnight at 37° C. This way, all genuinely attached bacterial cells are captured on the slide surface, and those of them still viable can proliferate and form colonies.

Figure 6:
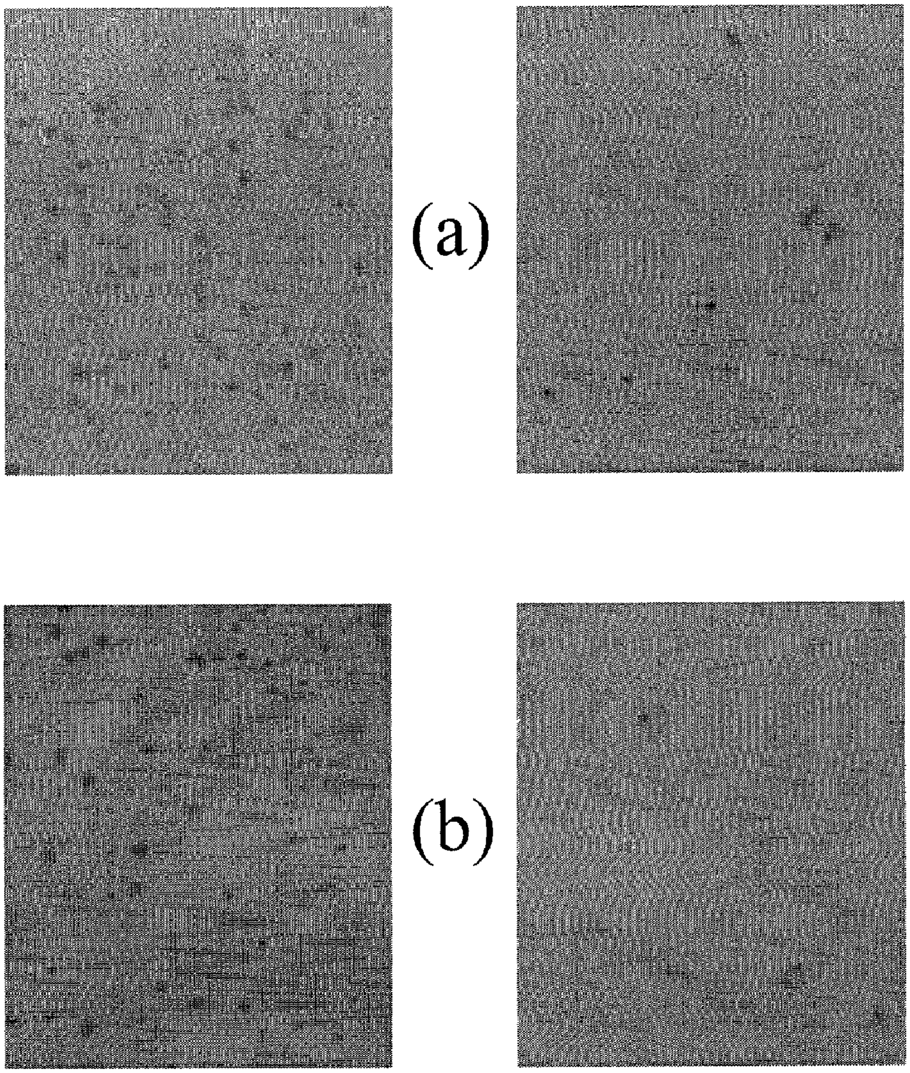
FIG. 6 depicts photographs of a commercial HDPE slide (left) and the hexyl-PVP-derivatized slide (right) onto which (a) *S. aureus* or (b) *E. coli* cells were allowed to adhere from aqueous PBS, pH 7.0, suspensions (approximately $10^6$ cells/mL of PBS), washed with PBS, and incubated under 1.5% agar in a bacterial growth medium at 37° C. overnight.

As seen in FIG. 6*a*, left, *S. aureus* cells allowed to adhere to an HDPE slide form numerous easily distinguishable colonies. Neither $SiO_2$— nor NH2— modified HDPE slides exhibited an appreciable decline in the number of bacterial colonies grown after the adhesion. However, as seen in FIG. 6*a*, right, the number of *S. aureus* colonies grown on a hexyl-PVP-modified HDPE slide plunged 98±1% (see also Table 4).

TABLE 4

The ability of hexyl-PVP covalently attached to various commercial polymer slides to kill waterborne bacteria on contact.

| | | Percentage of bacteria killed | | | | |
|---|---|---|---|---|---|---|
| Bacterium | Type | HDPE | LDPE | PP | nylon | PET |
| *S. aureus* | Gram (+) | 98 ± 1 | 99 ± 1 | 97 ± 2 | 97 ± 1 | 99 ± 1 |
| *E. coli* | Gram (−) | 97 ± 2 | 98 ± 2 | n.d. | 99 ± 1 | 98 ± 1 |

Suspensions of bacteria ($2 \times 10^6$ cells/mL for *S. aureus* and $4 \times 10^6$ cells/mL for *E. coli*) in PBS, pH 7.0, was allowed to adhere to the hexyl-PVP-modified polymer surfaces under shaking at 37° C. for 2 h. The slides were rinsed with sterile PBS, pH 7.0, shaken in sterile PBS at 37° C. for 1 h, rinsed again with the PBS, incubated under 1.5% agar in a bacterial growth medium overnight, and the colonies were counted. N.d. stands for "not determined" because adhered bacterial cells grow but do not form distinguishable colonies on the control slide. For other conditions, see the footnotes to Table 3.

It was further demonstrated that hexyl-PVP-derivatized LDPE, PP, nylon, and PET also can kill waterborne bacteria on contact. The data in Table 4 show that upon the derivatization (FIG. 4) the number of viable adhered *S. aureus* cells drops by 97 to 99% for all polymer slides. Likewise, the modified polymer slides were found to be effective against waterborne *E. coli*. As seen in FIG. 6*b*, left, *E. coli* cells adhered to an unmodified HDPE slide from an aqueous suspension grow a number of distinguishable colonies under the growth agar cover. The colonies on LDPE, nylon, and PET looked similar, while no colonies were distinguishable on PP. Upon the derivatization of HDPE with hexyl-PVP, the number of viable adhered *E. coli* cells plummeted 97±2%

(FIG. 6*b*, right, Table 4). The other modified polymers also displayed drastically lower numbers of adhered viable *E. coli* cells compared to the corresponding unmodified slides, with killing efficiencies of 98 to 99% observed for LDPE, PET, and nylon (Table 4, last line).

Since the experimental conditions for the determination of bactericidal properties of the hexyl-PVP-modified slides against waterborne bacteria were different from those for airborne ones, we again tested for release of the polycation from a slide into the medium. To this end, a hexyl-PVP-modified HDPE slide was incubated for 2 h in sterile PBS with shaking at 37° C., removed, and *S. aureus* cells were added to the remaining solution. The resulting suspension was again shaken at 37° C. for 2 h, and the number of viable bacterial cells was determined by spreading it on growth agar, followed by incubation at 37° C. overnight. The number of bacterial colonies observed, $(42\pm4)\cdot10^4$ per mL, coincided with that in the control $[(48\pm7)\cdot10^4$ per mL]. Hence there is no appreciable release of an antibacterial agent from the hexyl-PVP-modified HDPE slide during the bacterial adhesion experiment, and the waterborne bacteria must indeed be killed on contact with the derivatized surface.

Mechanism of Attacking Bacteria

Tethered amphipathic polycations described in this study and soluble cationic antimicrobials probably share a similar mechanism of attacking bacteria. Polycations, such as polymyxin B and antimicrobial cationic peptides of animals, displace the divalent cations that hold together the negatively charged surface of the lipopolysaccharide network, thereby disrupting the outer membrane of Gram-negative bacteria like *P. aeruginosa* and *E. coli* (Vaara, M. (1992) *Microbiol Rev.* 56, 395–411). This in itself might be sufficient for a lethal outcome. It is also possible that, having destroyed the outer membrane permeability barrier, the cationic groups of the tethered polymers further penetrate into the inner membrane, producing leakage. Such "self-promoted penetration" with the subsequent damage of the inner membrane has been described for polymyxin The action of immobilized polycations against the Gram-positive bacteria *S. aureus* and *S. epidermidis* probably requires penetration of the cationic groups across the thick cell wall to reach the cytoplasmic membrane. Bactericidal action of amphipathic cationic antiseptics, such as benzalkonium chloride or biguanidine chlorhexidine, against Gram-positive bacteria is due primarily to the disruption of the cytoplasmic membrane(Denton, G. W. (2001) in *Disinfection, Sterilization,* and *Preservation,* ed. Block, S. S.(Lippincott Williams & Wilkins, Philadelphia)). The cell wall of *S. aureus* is some 30 nm thick (Friedrich, C. L., Moyles, D., Beveridge, T. J. & Hancock, R. E. (2000) *Antimicrob. Agents Chemother.* 44, 2086–2092.); since the estimated average length of the N-hexylated PVP (Method A) is 19 nm, with some obviously being shorter and others longer, the latter could penetrate the cell wall.

Medical Applications

Such surface modifications can be readily performed with a number of other materials. A simple periodic washing would remove the dead deposited cells and rejuvenate such surfaces.

Any object placed in the body from outside it is susceptible to biological contamination with microorganisms and subsequent biofilm formation. Therefore, compounds according to the present invention can prevent such objects from becoming contaminated with microorganisms in the first place. Further, these technologies can be used to produce natural and synthetic materials resistant to contamination that are especially suited for replacing those objects that have already sustained infection, or that are intended for being placed in those anatomic sites where infections can be particularly devastating.

Naturally derived processed materials commonly are positioned in the body in order to provide a structure for ingrowth of the patient's own tissues. Examples include demineralized bone materials and hydroxyapatite. These materials are destined to be infiltrated or replaced entirely by the patient's tissue, during which time the exogenous material retains the desired shape or structural support in the affected area. These materials themselves are non-living and avascular. Colonization of these materials with microorganisms and biofilm formation can require their removal. If the material is removed, the shape or the structure that it is maintaining is destroyed and the progress made by tissue in growth is in vain. Application of compounds of the invention to these materials can enhance their resistance to biofilm formation and its consequences.

Certain naturally derived processed materials will be determined by artisans in these fields to especially suitable for the application or incorporation of compounds of the invention. A material can be contacted with the claimed compounds in a variety of ways including immersion and coating. In forms where the material has interstices, an AF compound can reside therein as a liquid or as a gel. Fibrillar preparations can permit the fibers to be coated with the compound. Solid articles such as reconstructive blocks of hydroxyapatite can be painted with a coating of the compound for additional protection. These temporary means of application are appropriate for these materials because they only reside in the body temporarily, to be resorbed or replaced.

Implantable medical devices, using artificial materials alone or in combination with naturally-derived materials, can be treated with compounds either by surface coating or by incorporation. Metals may be suitably treated with surface coats while retaining their biological properties. In certain embodiments of the present invention, metals may be treated with paints or with adherent layers of polymers or ceramics that incorporate the compounds of the invention. Certain embodiments treated in this manner may be suitable for orthopedic applications, for example, pins, screws, plates or parts of artificial joints. Methods for surface treatment of metals for biological use are well-known in the relevant arts. Other materials besides metals can be treated with surface coats of compounds according to the present invention as the medical application requires.

Implantable devices may comprise materials suitable for the incorporation of the instant claimed compounds. Embodiments whose components incorporate compounds of the invention can include polymers, ceramics and other substances. Materials fabricated from artificial materials can also be destined for resorption when they are placed in the body. Such materials can be called bioabsorbable. As an example, polyglycolic acid polymers can be used to fabricate sutures and orthopedic devices. Those of ordinary skill in these arts will be familiar with techniques for incorporating agents into the polymers used to shape formed articles for medical applications. AF agents can also be incorporated into glues, cements or adhesives, or in other materials used to fix structures within the body or to adhere implants to a body structure. Examples include polymethylmethacrylate and its related compounds, used for the affixation of orthopedic and dental prostheses within the body. The presence of the compounds of the instant invention can decrease biofilm formation in those structures in contact with the glue, cement, or adhesive. Alternatively, a compound of the invention can coat or can permeate the formed article. In these compositions, the formed article allows diffusion of the compound, or functional portion thereof, into the surrounding environment, thereby preventing fouling of the appliance itself. Microcapsules bearing compounds can also be imbedded in the material. Materials incorporating compounds are adaptable to the manufacture of a wide range of medical devices, some of which are disclosed below. Other examples will be readily apparent to those practitioners of ordinary skill in the art.

In one embodiment, compounds of the invention can be applied to or incorporated in certain medical devices that are intended to be left in position permanently to replace or restore vital functions. As one example, ventriculoatrial or ventriculoperitoneal shunts are devised to prevent cerebrospinal fluid from collecting in the brain of patients whose normal drainage channels are impaired. As long as the shunt functions, fluid is prevented from accumulating in the brain and normal brain function can continue. If the shunt ceases to function, fluid accumulates and compresses the brain, with potentially life-threatening effect. If the shunt becomes infected, it causes an infection to enter the central portions of the brain, another life-threatening complication. These shunts commonly include a silicone elastomer or another polymer as part of their fabrication. Silicones are understood to be especially suited for combination with compounds according to the present invention.

Another shunt that has life-saving import is a dialysis shunt, a piece of polymeric tubing connecting an artery and a vein in the forearm to provide the kidney failure patient a means by which the dialysis equipment can cleanse the bloodstream. Even though this is a high-flow conduit, it is susceptible to the formation of biofilms and subsequent infection. If a shunt becomes infected, it requires removal and replacement. Since dialysis may be a lifelong process, and since there are a limited number of sites where shunts can be applied, it is desirable to avoid having to remove one through infectious complications. Imbedding or otherwise contacting the compounds of the invention with the shunt material can have this desired effect.

Heart valves comprising artificial material are understood to be vulnerable to the dangerous complication of prosthetic valve endocarditis. Once established, it carries a mortality rate as high as 70%. Biofilms are integrally involved in the development of this condition. At present, the only treatment for established contamination is high-dose antibiotic therapy and surgical removal of the device. The contaminated valve must be immediately replaced, since the heart cannot function without it. Because the new valve is being inserted in a recently contaminated area, it is common for prosthetic valve endocarditis to affect the replacement valve as well. Artificial heart valves comprised of the compounds of the invention may reduce the incidence of primary and recurrent prosthetic valve endocarditis. Compounds of the invention can be applied to the synthetic portions or the naturally-derived portions of heart valves.

Pacemakers and artificial implantable defibrillators commonly comprise metallic parts in combination with other synthetic materials. These devices, which may be coated with a polymeric substance such as silicone are typically implanted in subcutaneous or intramuscular locations with wires or other electrical devices extending intrathoracically or intravascularly. If the device becomes colonized with microorganisms and infected, it must be removed. A new device can be replaced in a different location, although there are a finite number of appropriate implantation sites on the body. Devices comprising the compounds of the invention may inhibit contamination and infection, or substantially reduce the risk thereof.

Devices implanted into the body either temporarily or permanently to pump pharmacological agents into the body can comprise metallic parts in combination with other synthetic materials. Such devices, termed infusion pumps, can be entirely implanted or can be partially implanted. The device may be partially or entirely covered with a polymeric substance, and may comprise other polymers used as conduits or tubes. Incorporating AF agents according to the present invention into the coating materials imposed upon these devices or into the materials used for the devices themselves, their conduits or their tubing may inhibit their contamination and infection.

Equally lifesaving are the various vascular grafting prostheses and stents intended to bypass blocked arteries or substitute for damaged arteries. Vascular grafting prostheses, made of Teflon, dacron, Gore-tex®, expanded polytetrafluoroethylene (e-PTFE), and related materials, are available for use on any major blood vessel in the body. Commonly, for example, vascular grafting prostheses are used to bypass vessels in the leg and are used to substitute for a damaged aorta. They are put in place by being sewn into the end or the side of a normal blood vessel upstream and downstream of the area to be bypassed or replaced, so that blood flows from a normal area into the vascular grafting prosthesis to be delivered to other normal blood vessels. Stents comprising metallic frames covered with vascular grafting prosthesis fabric are also available for endovascular application, to repair damaged blood vessels.

Suture material used to anchor vascular grafting prostheses to normal blood vessels or to sew vessels or other structures together can also harbor infections. Sutures used for these purposes are commonly made of prolene, nylon or other monofilamentous nonabsorbable materials. An infection that begins at a suture line can extend to involve the vascular grafting prosthesis. Suture materials comprising a compound of the invention would have increased resistance to infection.

A general principle of surgery is that when a foreign object becomes infected, it most likely needs to be removed so that the infection can be controlled. For example, when sutures become infected, they may need to be surgically removed to allow the infection to be controlled. Any area where surgery is performed is susceptible to a wound infection. Wound infections can penetrate to deeper levels of the tissues to involve foreign material that has been used as part of the operation. As an example, hernias are commonly repaired by suturing a plastic screening material called mesh in the defect. A wound infection that extends to the area where the mesh has been placed can involve the mesh itself, requiring that the mesh be removed. Surgical meshes comprising a compound of the invention can have increased resistance to infection. Surgical meshes are made of substances like Gore-tex®, teflon, nylon and Marlex®. Surgical meshes are used to close deep wounds or to reinforce the enclosure of body cavities. Removing an infected mesh can leave an irreparable defect, with life-threatening consequences. Avoiding infection of these materials is of paramount importance in surgery. Materials used for meshes and related materials can be formulated to include the claimed compounds of the instant invention.

Certain implantable devices intended to restore structural stability to body parts can be advantageously treated with the instant claimed compounds. A few examples follow, and others will be readily identified by ordinary skilled artisans. Implantable devices, used to replace bones or joints or teeth, act as prostheses or substitutes for the normal structure present at that anatomic site. Metallics and ceramics are commonly used for orthopedic and dental prostheses. Implants may be anchored in place with cements like polymethylmethacrylate. Prosthetic joint surfaces can be fabricated from polymers such as silicones or teflon. Entire prosthetic joints for fingers, toes or wrists can be made from polymers.

Medical prostheses comprising compounds of the invention would be expected to have reduced contamination and subsequent local infection, thereby obviating or reducing the need to remove the implant with the attendant destruction of local tissues. Destruction of local tissues, especially bones and ligaments, can make the tissue bed less hospitable for supporting a replacement prosthesis. Furthermore, the presence of contaminating microorganisms in surrounding tissues makes recontamination of the replacement prosthesis easily possible. The effects of repeated contamination and infection of structural prosthetics is significant: major reconstructive surgery may be required to rehabilitate the area in the absence of the prosthesis, potentially including free bone transfers or joint fusions. Furthermore, there is no guarantee that these secondary reconstructive efforts will not meet with infectious complications as well. Major disability, with possible extremity amputation, is the outcome from contamination and infection of a structural prosthesis.

Certain implantable devices are intended to restore or enhance body contours for cosmetic or reconstructive applications. A well-known example of such a device is the breast implant, a gel or fluid containing sac made of a silicone elastomer. Other polymeric implants exist that are intended for permanent cosmetic or reconstructive uses. Solid silicone blocks or sheets can be inserted into contour defects. Other naturally occurring or synthetic biomaterials are available for similar applications. Craniofacial surgical reconstruction can involve implantable devices for restoring severely deformed facial contours in addition to the techniques used for restructuring natural bony contours. These devices, and other related devices well-known in the field, are suitable for coating with or impregnation with sulfate ester AF agents to reduce their risk of contamination, infection and subsequent removal.

Tissue expanders are sacs made of silicone elastomers adapted for gradual filling with a saline solution, whereby the filling process stretches the overlying tissues to generate an increased area of tissue that can be used for other reconstructive applications. Tissue expanders can be used, for example, to expand chest wall skin and muscle after mastectomy as a step towards breast reconstruction. Tissue expanders can also be used in reconstructing areas of significant skin loss in bum victims. A tissue expander is usually intended for temporary use: once the overlying tissues are adequately expanded, they are stretched to cover their intended defect. If a tissue expander is removed before the expanded tissues are transposed, though, all the expansion gained over time is lost and the tissues return nearly to their pre-expansion state. The most common reason for premature tissue expander removal is infection. These devices are subjected to repeated inflations of saline solution, introduced percutaneously into remote filling devices that communicate with the expander itself. Bacterial contamination of the device is thought to occur usually from the percutaneous inflation process. Once contamination is established and a biofilm forms, local infection is likely. Expander removal, with the annulment of the reconstructive effort, is needed to control the infection. A delay of a number of months is usually recommended before a new tissue expander can be inserted in the affected area. The silicone elastomer used for these devices is especially suitable for integrating with sulfate ester AF agents. Use of these agents in the manufacture of these articles may reduce the incidence of bacterial contamination, biofilm development and subsequent local infection.

Insertable devices include those objects made from synthetic materials applied to the body or partially inserted into the body through a natural or an artificial site of entry. Examples of articles applied to the body include contact lenses and stoma appliances. An artificial larynx is understood to be an insertable device in that it exists in the airway, partially exposed to the environment and partially affixed to the surrounding tissues. An endotracheal or tracheal tube, a gastrostomy tube or a catheter are examples of insertable devices partially existing within the body and partially exposed to the external environment. The endotracheal tube is passed through an existing natural orifice. The tracheal tube is passed through an artificially created orifice. Under any of these circumstances, the formation of biofilm on the device permits the ingress of microorganisms along the device from a more external anatomic area to a more internal anatomic area. The ascent of microorganisms to the more internal anatomic area commonly causes local and systemic infections.

As an example, biofilm formation on soft contact lenses is understood to be a risk factor for contact-lens associated corneal infection. The eye itself is vulnerable to infections due to biofilm production. Incorporating an antifouling agent in the contact lens itself and in the contact lens case can reduce the formation of biofilms, thereby reducing risk of infection. Sulfate ester AF agents can also be incorporated in ophthalmic preparations that are periodically instilled in the eye.

As another example, biofilms are understood to be responsible for infections originating in tympanostomy tubes and in artificial larynxes. Biofilms further reside in tracheostomy tubes and in endotracheal tubes, permitting the incursion of pathogenic bacteria into the relatively sterile distal airways of the lung. These devices are adaptable to the incorporation or the topical application of sulfate ester AF agents to reduce biofilm formation and subsequent infectious complications.

As another example, a wide range of vascular catheters are fabricated for vascular access. Temporary intravenous catheters are placed distally, while central venous catheters are placed in the more proximal large veins. Catheter systems can include those installed percutaneously whose hubs are external to the body, and those whose access ports are buried beneath the skin. Examples of long-term central venous catheters include Hickman catheters and Port-a-caths. Catheters permit the infusion of fluids, nutrients and medications; they further can permit the withdrawal of blood for diagnostic studies or the transfusion of blood or blood products. They are prone to biofilm formation, increasingly so as they reside longer within a particular vein. Biofilm formation in a vascular access device can lead to the development of a blood-borne infection as planktonic organisms disseminate from the biofilm into the surrounding bloodstream. Further, biofilm formation can contribute to the occlusion of the device itself, rendering it non-functional. If the catheter is infected, or if the obstruction within it cannot be cleared, the catheter must be removed. Commonly, patients with these devices are afflicted with serious medical conditions. These patients are thus poorly able to tolerate the removal and replacement of the device. Furthermore, there are only a limited number of vascular access sites. A patient with repeated catheter placements can run out of locations where a new catheter can be easily and safely placed. Incorporation of sulfate ester AF agents within catheter materials or application of these agents to catheter materials can reduce fouling and biofilm formation, thereby contributing to prolonged patency of the devices and minimizing the risk of infectious complications.

As another example, a biliary drainage tube is used to drain bile from the biliary tree to the body's exterior if the normal biliary system is blocked or is recovering from a surgical manipulation. Drainage tubes can be made of plastics or other polymers. A biliary stent, commonly fabricated of a plastic material, can be inserted within a channel of the biliary tree to keep the duct open so that bile can pass through it. Biliary sludge which forms as a result of bacterial adherence and biofilm formation in the biliary system is a recognized cause of blockage of biliary stents. Pancreatic stents, placed to hold the pancreatic ducts open or to drain a pseudocyst of the pancreas, can also become blocked with sludge. Biofilms are furthermore implicated in the ascent of infections into the biliary tree along a biliary drainage tube. Ascending infections in the biliary tree can result in the dangerous infectious condition called cholangitis. Incorporation of compounds of the invention in the materials used to form biliary drainage tubes and biliary stents can reduce the formation of biofilms, thereby decreasing risk of occlusions and infections.

As another example, a peritoneal dialysis catheter is used to remove bodily wastes in patients with renal failure by using fluids instilled into and then removed from the peritoneal cavity. This form of dialysis is an alternative to hemodialysis for certain renal failure patients. Biofilm formation on the surfaces of the peritoneal dialysis catheter can contribute to blockage and infection. An infection entering the peritoneal cavity is termed a peritonitis, an especially dangerous type of infection. Peritoneal dialysis catheters, generally made of polymeric materials like polyethylene, can be coated with or impregnated with sulfate ester AF agents to reduce the formation of biofilms.

As yet another example, a wide range of urological catheters exist to provide drainage of the urinary system. These catheters can either enter the natural orifice of the urethra to drain the bladder, or they can be adapted for penetration of the urinary system through an iatrogenically created insertion site. Nephrostomy tubes and suprapubic tubes represent examples of the latter. Catheters can be positioned in the ureters on a semipermanent basis to hold the ureter open; such a catheter is called a ureteral stent. Urological catheters can be made from a variety of polymeric products. Latex and rubber tubes have been used, as have silicones. All catheters are susceptible to biofilm formation. This leads to the problem of ascending urinary tract infections, where the biofilm can spread proximally, carrying pathogenic organisms, or where the sessile organisms resident in the biofilm can propagate planktonic organisms that are capable of tissue and bloodstream invasion. Organisms in the urinary tract are commonly Gram-negative bacteria capable of producing life-threatening bloodstream infections if they spread systemically. Infections wherein these organisms are restricted to the urinary tract can nonetheless be dangerous, accompanied by pain and high fever. Urinary tract infections can lead to kidney infections, called pyelonephritis, that can jeopardize the function of the kidney. Incorporating sulfate ester AF agents can inhibit biofilm formation and may reduce the likelihood of these infectious complications.

A further complication encountered in urological catheters is encrustation, a process by which inorganic compounds comprising calcium, magnesium and phosphorous are deposited within the catheter lumen, thereby blocking it. These inorganic compounds are understood to arise from the actions of certain bacteria resident in biofilms on catheter surfaces. Reducing biofilm formation by the action of sulfate ester AF agents may contribute to reducing encrustation and subsequent blockage of urological catheters.

Other catheter-like devices exist that can be treated with AF agents. For example, surgical drains, chest tubes, hemovacs and the like can be advantageously treated with materials to impair biofilm formation. Other examples of such devices will be familiar to ordinary practitioners in these arts.

Materials applied to the body can advantageously employ the AF compounds disclosed herein. Dressing materials can themselves incorporate the AF compounds, as in a film or sheet to be applied directly to a skin surface. Additionally, AF compounds of the instant invention can be incorporated in the glue or adhesive used to stick the dressing materials or appliance to the skin. Stoma adhesive or medical-grade glue may, for example, be formulated to include an AF agent appropriate to the particular medical setting. Stoma adhesive is used to adhere stoma bags and similar appliances to the skin without traumatizing the skin excessively. The presence of infectious organisms in these appliances and on the surrounding skin makes these devices particularly appropriate for coating with AF agents, or for incorporating AF agents therein. Other affixation devices can be similarly treated. Bandages, adhesive tapes and clear plastic adherent sheets are further examples where the incorporation of an AF agent in the glue or other adhesive used to affix the object, or incorporation of an AF agent as a component of the object itself, may be beneficial in reducing skin irritation and infection.

These above examples are offered to illustrate the multiplicity of applications of compounds of the invention in medical devices. Other examples will be readily envisioned by skilled artisans in these fields. The scope of the present invention is intended to encompass all those surfaces where the presence of fouling has adverse health-related consequences. The examples given above represent embodiments where the technologies of the present invention are understood to be applicable. Other embodiments will be apparent to practitioners of these and related arts. Embodiments of the present invention can be compatible for combination with currently employed antiseptic regimens to enhance their antimicrobial efficacy or cost-effective use. Selection of an appropriate vehicle for bearing a compound of the invention will be determined by the characteristics of the particular medical use. Other examples of applications in medical environments to promote antisepsis will be readily envisioned by those of ordinary skill in the relevant arts.

EXEMPLIFICATION

The invention now being generally described, it will be more readily understood by reference to the following examples, which are included merely for purposes of illustration of certain aspects and embodiments of the present invention, and are not intended to limit the invention.

Surface Derivatization

Example 1

Method A

A $NH_2$-glass slide (aminopropyltrimethoxysilane-coated microscopic slides) was placed in 90 mL of dry dichloromethane containing 1 mL of triethylamine. After cooling to 4° C., 10 mL of acryloyl chloride was added, and the reaction mixture was stirred in a cold room overnight and then at room temperature for 2 h. The acylated $NH_2$-glass slides were rinsed with a methanol/triethylamine mixture (1:1, v/v) and methanol. As judged from the determination of the $NH_2$ groups on the glass slide surface before ($6.6\pm0.1\times10^{-10}$ mol/cm$^2$) and after ($3.3\pm0.2\times10^{-10}$ mol/cm$^2$) the acryloylation using the picric acid titration (17), some half of the surface-bound amino groups reacted with acryloyl chloride. The glass-bonded acryloyl moieties were then copolymerized with 4-vinylpyridine. Perchloric acid (90 mL of a 20% solution in water) was degassed, and 30 mg Of $Ce(SO_4)_2$ was added under argon. After 1 h of stirring, an acryloylated glass slide was placed in this solution, 15 mL of freshly distilled 4-vinylpyridine was added under argon, and the reaction mixture was stirred at room temperature for 3 h. PVP not chemically attached to the slide was washed off with pyridine, N,N-dimethylformide, and methanol. Immediately thereafter, the slide with the attached PVP was placed in a 10% (v/v) solution of an alkyl bromide in nitromethane. The reaction mixture was then stirred at 75° C. for 72 h, after which time more than 90% of the pyridine rings were N-alkylated (19). The resultant polycation-derivatized PVP-slide was rinsed with methanol and distilled water and air dried.

Example 2

Method B

A $NH_2$-glass slide was immersed in a mixture containing 9 mL of 1,4-dibromobutane, 90 mL of dry nitromethane, and 0.1 mL of triethylamine. After stirring at 60° C. for 2 h, the slide was removed, thoroughly rinsed with nitromethane, air dried, and placed in a solution of 9 g of PVP (molecular weight of 60,000 or 160,000 g/mol) in 90 mL of nitromethane/hexyl bromide (10:1, v/v). After stirring the reaction mixture at 75° C. for 24 h, the slide was rinsed with acetone, thoroughly washed with methanol (to remove the non-attached polymer), and air dried. According to the literature (14), more than 96% of the pyridine rings of PVP should be N-alkylated under these conditions.

Surface Analysis

Example 3

A chemically modified glass slide was immersed in a 1% solution of fluorescein (Na salt) in distilled water for 5 min. Under these conditions, the dye binds to quaternary amino groups (20), but not to tertiary or primary ones (we found that PVP-modified or $NH_2$-glass slides do not adsorb fluorescein). After rinsing with distilled water, a stained slide was placed in 25 mL of the 0.1% detergent cetyltrimethylammonium chloride in distilled water and shaken for 10 min to desorb the dye. The absorbance of the of the resultant aqueous solution was measured at 501 nm (after adding 10% of a 100 mM aqueous phosphate buffer, pH 8.0). The independently determined extinction coefficient of fluorescein in this solution was found to be 77 mM$^{-1}$ cm$^{-1}$.

From staining different hexyl-PVP-films (160,000 g/mol, degree of alkylation >95%) with a known polymer content, the stoichiometry of fluorescein binding was found to be approximately 1 dye molecule per 7 hexyl-PVP monomer units. The following amounts of the attached hexyl-PVP were determined (assuming that more than 90% of the polymer is hexylated): 5.8±3.0 μg/cm$^2$ (method A); 2.8±1.0 μg/cm$^2$ (method B, PVP with $M_W$=160,000 g/mol); and 0.4±0.05 μg/cm$^2$ (method B, PVP with $M_W$=60,000 g/mol). In the case of hexyl-PVP immobilized by method A, the minimal chain length of the attached polycation was estimated to be 61±30 monomer units.

Antimicrobial Susceptibility Determination

Example 4

A suspension (100 μL) of *Staphylococcus aureus* (ATCC, strain 33807), *Staphylococcus epidermidis* (wild type), *Pseudomonas aeruginosa* (wild type), or *Escherichia coli* (ZK 605) in 0.1 M aqueous PBS buffer (pH 7.0, approximately $10^{11}$ cells/mL) was added to 50 mL of a yeast-dextrose broth (prepared as described by Cunliffe et al. (21)) in a sterile Erlenmeyer flask. The suspension was incubated at 37° C. with shaking at 200 rpm for 6–8 h. After centrifugation (2,700 rpm, 10 min), the bacterial cells were washed with, and re-suspended in, distilled water at a concentration of $10^6$ cells per mL ($10^7$ in the case of *E. coli*).

A bacterial suspension was then sprayed onto a glass slide (or another surface) in a fume hood using a commercial chromatography sprayer (VWR) (spray rate of approximately 10 mL/min). After drying for 2 min under air, the slide was placed in a petri dish, and then growth agar (0.7% agar in a yeast-dextrose broth, autoclaved, and cooled to 37° C.) was added. The petri dish was closed, sealed, and incubated at 37° C. overnight.

Example 5

The bacteria were suspended in distilled water and sprayed onto the surface of a slide to simulate the deposition of airborne bacteria—a common method of spreading bacterial infections generated, for example, by talking, sneezing, coughing, or just breathing. To determine the number of viable bacterial cells on the infected surface, the slide, following a 2-min air drying, was incubated under growth agar; the bacteria able to proliferate form countable colonies under these conditions. Infectious Gram-positive bacterium *Staphylococcus aureus* was used for the initial studies. Next, a $NH_2$-glass slide was acylated with acryloyl chloride to introduce double bonds, followed by copolymerization with 4-vinylpyridine. Such an immobilized PVP was found to afford approximately the same number of viable *S. aureus* cells after spraying the bacterial suspension onto its surface as a plain $NH_2$-glass slide. The final step was to introduce positive charges into the PVP chains attached to glass. To this end, the polymer's pyridine rings were N-alkylated by seven linear alkyl bromides (with chain lengths varying from propyl to hexadecyl). The resultant slides were examined with respect to their ability to kill on contact *S. aureus* cells sprayed on them. As seen in FIG. 2, propylated, butylated, hexylated, and octylated immobilized PVP chains were effective in markedly reducing the number of viable bacterial cells, with the most effective, hexyl-PVP affording a 94±4% reduction. (See right portion of FIG. 1).

Example 6

Using a glass slide surface modified with hexyl-PVP (henceforth referred to as that prepared by method A), we then tested the bactericidal effect of this surface toward another Gram-positive bacterium, *S. epidermidis,* as well as two Gram-negative bacteria, *E. coli* and *P. aeruginosa.* The first two formed colonies of the same size as *S. aureus* (FIG. 1, left portion) when sprayed on $NH_2$-glass slides, whereas the colonies of *P. aeruginosa* were larger but still distinguishable. As seen in Table 1 (method A), the number of colonies all three bacteria formed after spraying onto hexyl-PVP-slides dropped more than 100-fold compared to the plain $NH_2$-glass.

Suspensions ($10^6$ cells/mL for the first 3 bacteria and $10^7$ cells/mL for the last one) of bacteria in distilled water were sprayed on hexyl-PVP-modified glass surfaces, air dried for 2 min, incubated under 0.7% agar in a bacterial growth medium overnight, and the colonies were counted. The number of viable cells obtained in the same manner with commercial $NH_2$-glass slides was used as a standard (i.e., 0% of the bacteria killed).

Example 7

Antibacterial properties of a PVP-based polycation immobilized onto glass slides were analyzed in different procedure using a NH2-glass slide was alkylated with 1,4-dibromobutane to introduce reactive bromobutyl groups, which were subsequently used for the attachment of PVP. The resultant surface was not able to kill *S. aureus* cells upon spraying. To increase the positive charge of the attached PVP chains, the chains were further N-alkylated them with hexyl bromide After *S. aureus* cells were sprayed, air dried, and cultured, the resultant hexyl-PVP-slides (henceforth referred to as those prepared by method B) looked essentially the same as shown in the right portion of FIG. 1. Compared to a $NH_2$-glass slide, 94±3% of the deposited *S. aureus* cells were killed (the last column, 1 st line, of Table 1).

Suspensions ($10^6$ cells/mL for the first 3 bacteria and $10^7$ cells/mL for the last one) of bacteria in distilled water were sprayed on hexyl-PVP-modified glass surfaces, air dried for 2 min, incubated under 0.7% agar in a bacterial growth medium overnight, and the colonies were counted. The number of viable cells obtained in the same manner with commercial $NH_2$-glass slides was used as a standard (i.e., 0% of the bacteria killed).

Surface Derivatization

Example 8

A HDPE slide (7.5×2.5 cm, Polymer Plastics Co., Reno, Nev.) was sonicated in isopropyl alcohol for 5 min, rinsed with that solvent, and dried at 80° C. for 30 min. Next, the front (oxidizing) part of the flame of a hand-held burner (SurA Instruments GmbH, Jena, Germany) was fanned over the slide surface for 15 s, and the slide was stored under air overnight. The compressed gas mixture of the burner contained 0.6% (v/v) tetramethylsilane in a propane/butane (7:3, v/v) mixture (Pyrosil®). The $SiO_2$-coated HDPE slide was then placed into a 20% solution of 3-aminopropyltriethoxysilane (Aldrich Chemical Co., Milwaukee, Wis.) in dry toluene, incubated with stirring at room temperature for 3 h, rinsed with toluene and methanol, and dried under air overnight. Bisse, E., Scholer, A. & Vonderschmitt, D. J. A new method for coupling glucose dehydrogenase to glass tubes activated with titanium tetrachloride. *FEBS Lett.* 138, 316–318 (1982). The $NH_2$-functionalized HDPE slide was then treated with a mixture of 10 mL of 1,4-dibromobutane, 0.1 mL of triethylamine, and 90 mL of nitromethane with stirring at 60° C. for 5 h and rinsed with nitromethane, followed by addition of a freshly prepared solution of 9 g of PVP (molecular weight of 160,000 g/mol) in 81 mL of nitromethane and 10 mL of 1-bromohexane (all from Aldrich). After 9 h of stirring at 75° C., the slide was thoroughly rinsed with methanol and distilled water, and dried under air. Slides (all 7.5×2.5 cm in size) of LDPE (Polymer Plastics Co.), PP, nylon (type 6/6) (Plastic Material Co., Cleveland, Ohio), and PET (Wheaton, Millville, N.J.) were derivatized following the same protocol, except that PET in the last step was treated at 60° C. instead of 75° C.

Surface Analysis

Example 9

The X-ray photoelectron spectrum of the $SiO_2$-coated HDPE slide was recorded using a Kratos Axis Ultra instrument (Kratos Analytical, New York, N.Y.) using a 150 W A1 Kα monochromator source.

Example 10

A hexyl-PVP-derivatized slide was placed in a 1% fluorescein (Sigma Chemical Co., St. Louis, Mo.) solution in distilled water, shaken for 5 min, thoroughly rinsed with water, and placed in a 0.25% aqueous solution of cetyltrimethylammonium chloride (Aldrich). After shaking for 5 min, 10% (v/v) of 0.1 M aqueous phosphate buffer, pH 8.0, was added to the solution, the absorbance was measured at 501 nm, and the number of pyridinium groups on the surface was calculated as described earlier. Tiller, J. C., Liao, C.-J., Lewis, K. & Klibanov, A. M. Designing surfaces that kill bacteria on contact. *Proc. Natl. Acad. Sci. U.S.A.* 98, 5981–5985 (2001).

Antimicrobial Potency Determination

Example 11

Bacteria were cultivated by adding a suspension (100 μL) of *S. aureus* (strain 33807, ATCC, Manassas, Va.) or *E. coli* (strain ZK 650, provided by Dr. Gary Bonner, Harvard Medical School) in 0.1 M aqueous PBS buffer, pH 7.0 (approximately $10^{11}$ cells/mL) to 50 mL of a yeast-dextrose broth (prepared as described by Cunliffe et al.) in a sterile Erlenmeyer flask. Cunliffe, D., Smart, C. A., Alexander, C. & Vulfson, E. N. Bacterial adhesion at synthetic surfaces. *Appl. Environ. Microbiol.* 165, 4995–5002 (1999). The suspension was incubated at 37° C. with shaking at 200 rpm for 6–8 h.

The ability of surfaces to kill airborne bacteria was tested as described earlier. Tiller, J. C., Liao, C.-J., Lewis, K. & Klibanov, A. M. Designing surfaces that kill bacteria on contact. *Proc. Natl. Acad. Sci. U.S.A.* 98, 5981–5985 (2001). Bacterial cells were centrifuged at 2,700 rpm for 10 min, washed with distilled water, and re-suspended at a concentration of $10^6$ cells per mL for *S. aureus* and $10^5$ for *E. coli.* The bacterial cell concentration was assessed assuming that the optical density of 1.0 at 540 nm is equivalent to approximately $10^9$ cells per mL. Hogt, A. H., Dankert, J. & Feijen, J. Adhesion of coagulase-negative staphylococci to methacrylate polymers and copolymers. *J. Biomed. Mater. Res.* 20, 533–545 (1986). A bacterial suspension was then sprayed onto a polymer slide in a fume hood using a commercial chromatography sprayer (VWR, Boston, Mass.) (spraying rate of approximately 10 mL/min). After drying for 2 min under air, the slide was placed in a Petri dish, and growth agar (0.7% agar in yeast-dextrose broth, autoclaved, and cooled to 37° C.) was added. The dish was closed, sealed, and incubated at 37° C. overnight. The grown bacterial colonies were counted on a light box (Picker International, Cleveland, Ohio) which magnifies the contrast between colonies and polymer slide. In the case of nylon, the bacterial colonies were stained after the incubation: 1 mg of Crystal Violet (Sigma) was dissolved in 100 mL of distilled water and added onto the growth agar covering the infected slide until the surface was completely wetted. This procedure was repeated after 2 h; the stained colonies were visible within 5 h.

When polymers were tested against waterborne bacteria, bacterial cells were centrifuged at 2,700 rpm for 10 min, washed twice with PBS at pH 7.0, re-suspended in the same buffer, and diluted to $2 \cdot 10^6$ cells per mL of PBS ($4 \cdot 10^6$ in the case of *E. coli*). A plastic slide was placed in 45 mL of this suspension, incubated with shaking at 200 rpm and 37° C. for 2 h, washed three times by immersing the slide in the sterile PBS, immediately covered with a slab cut out of the solid growth agar (1.5% agar in the bacterial growth medium, autoclaved, poured into a Petri dish, and dried under reduced pressure at room temperature overnight), and incubated in a sealed Petri dish at 37° C. overnight. The bacterial colonies were counted as described above.

Example 12

Polymer Surfaces Derivatized with Poly(vinyl-N-hexylpyridinium) kill Airborne, Waterborne, and Deposited Bacteria A facile methodology has been developed for covalently derivatizing the surfaces of common materials with a designed antibacterial polycation, poly(vinyl-N-pyridinium bromide), wherein the first, key step involves surface coating with a nanolayer of silica. Various commercial synthetic polymers derivatized in this manner become bactericidal—they kill up to 99% of deposited, whether through air or water, Gram-positive and Gram-negative bacteria on contact.

We have discovered a novel, non-release strategy for creating bactericidal surfaces which involves covalent coating with long hydrophobic polycationic chains; critically, the latter must be fine-tuned with respect to charge and hydrophobicity to resist, by means of electrostatic repulsion, hydrophobic interchain aggregation and yet be able to penetrate bacterial cell membranes. As a result, glass slides covalently modified with poly(vinyl-N-hexylpyridinium bromide) (hexyl-PVP) were found to kill up to >99% of airborne bacteria. In this Example, we demonstrate a greatly extended range of such bactericidal materials, including common synthetic polymers. In doing so, a general surface coating/derivatization procedure has been discovered that will be applicable to most materials regardless of their nature. Specifically, five representative, inherently nonbactericidal, commercial polymers derivatized with hexyl-PVP have been demonstrated to kill 90 to 99% of Gram-positive and Gram-negative bacteria deposited, through either air or water, onto their surfaces.

Materials

Fluorescein (Na salt) and Crystal Violet were purchased from Sigma Chemical Co. 3-Aminopropyltriethoxysilane, 1-bromohexane, cetyltrimethylammonium chloride, poly(4-vinylpyridine) (PVP) (molecular weight of 160 kg/mol), and all other chemicals used in this work (analytical grade or purer) were obtained from Aldrich Chemical Co. and used without further purification. High-density polyethylene (HDPE), low-density polyethylene (LDPE), polypropylene (PP), and nylon 6/6 were supplied by Polymer Plastics Co. (Reno, Nev.), and poly(ethylene terephthalate) (PET) by Wheaton (Millville, N.J.). A hand-held burner containing 0.6% (v/v) tetramethylsilane in a propane/butane (7:3, v/v) mixture (Pyrosil®) was from SurA Instruments GmbH (Jena, Germany).

Surface Derivatization

A HDPE slide (7.5×2.5 cm) was sonicated in isopropyl alcohol for 5 min, rinsed with that solvent, and dried at 80° C. for 30 min. Next, the front (oxidizing) part of the flame of a hand-held burner was fanned over the slide surface for 15 s, and the slide was stored under air overnight. The $SiO_2$-coated HDPE slide was then placed into a 20% solution of 3-aminopropyltriethoxysilane in dry toluene, incubated with stirring at room temperature for 3 h, rinsed with toluene and methanol, and dried under air overnight (Bisse et al., 1982). The $NH_2$-functionalized HDPE slide was then treated with a mixture of 10 mL of 1,4-dibromobutane, 0.1 mL of triethylamine, and 90 mL of nitromethane with stirring at 60° C. for 5 h and rinsed with nitromethane, followed by addition of a freshly prepared solution of 9 g of PVP in 81 mL of nitromethane and 10 mL of 1-bromohexane. After 9 h of stirring at 75° C., the slide was thoroughly rinsed with methanol and distilled water and dried under air. Slides (all 7.5×2.5 cm in size) of LDPE, PP, nylon, and PET were derivatized following the same protocol, except that PET in the last step was treated at 60° C. instead of 75° C.

X-ray Photoelectron Spectroscopy

The X-ray photoelectron spectrum of the $SiO_2$-coated HDPE slide was recorded using a Kratos Axis Ultra instrument (Kratos Analytical, N.Y.) using a 150 W A1 Kα monochromator source.

Titration of Surface Pyridinium Groups

A hexyl-PVP-derivatized slide was placed in a 1% fluorescein solution in distilled water, shaken for 5 min, thoroughly rinsed with water, and placed in a 0.25% aqueous solution of cetyltrimethylammonium chloride. After shaking for 5 min, 10% (v/v) of 0.1 M aqueous phosphate buffer, pH 8.0, was added to the solution, the absorbance was measured at 501 nm, and the number of pyridinium groups on the surface was calculated as described earlier.

Antimicrobial Potency Determination

Bacteria were cultivated by adding a suspension (100 μL) of *S. aureus* (strain 33807, ATCC, Manassas, Va.) or *E. coli* (strain ZK 650, provided by Dr. Gary Bonner, Harvard Medical School) in 0.1 M aqueous PBS buffer, pH 7.0 (approximately $10^{11}$ cells/mL) to 50 mL of a yeast-dextrose broth (prepared as described by Cunliffe et al., 1999) in a sterile Erlenmeyer flask. The suspension was shaken at 200 rpm and 37° C. for 6–8 h.

The ability of surfaces to kill airborne bacteria was tested as described earlier (Tiller et al., 2001). Bacterial cells were centrifuged at 2,700 rpm for 10 min, washed with distilled water, and re-suspended at a concentration of $10^6$ cells per mL for *S. aureus* and $10^5$ for *E. coli*. The bacterial cell concentration was assessed assuming that the optical density of 1.0 at 540 nm is equivalent to approximately $10^9$ cells per mL (Hogt et al., 1986). A bacterial suspension was then sprayed onto a polymer slide in a fume hood using a commercial chromatography sprayer (VWR, Boston, Mass.) (spraying rate of approximately 10 mL/min). After drying for 2 min under air, the slide was placed in a Petri dish, and growth agar (0.7% agar in yeast-dextrose broth, autoclaved, and cooled to 37° C.) was added. The dish was closed, sealed, and incubated at 37° C. overnight. The grown bacterial colonies were counted on a light box (Picker International, Cleveland, Ohio) which magnifies the contrast between colonies and polymer slide. In the case of nylon, the bacterial colonies were stained after the incubation: 1 mg of Crystal Violet was dissolved in 100 mL of distilled water and added onto the growth agar covering the infected slide until the surface was completely wetted. This procedure was repeated after 2 h; the stained colonies were visible within 5 h.

When polymers were tested against waterborne bacteria, bacterial cells were centrifuged at 2,700 rpm for 10 min, washed twice with PBS (pH 7.0), re-suspended in the same buffer, and diluted to $2 \cdot 10^6$ cells per mL of PBS ($4 \cdot 10^6$ in the case of *E. coli*). A plastic slide was placed in 45 mL of this suspension, shaken at 200 rpm and 37° C. for 2 h, washed three times by immersing the slide in the sterile PBS, immediately covered with a slab cut out of the solid growth agar (1.5% agar in the bacterial growth medium, autoclaved, poured into a Petri dish, and dried under reduced pressure at room temperature overnight), and incubated in a sealed Petri dish at 37° C. overnight. The bacterial colonies were counted as described above.

Results and Discussion

Since it would be desirable to make numerous diverse objects bactericidal, we selected a surface derivatization approach potentially applicable to any material. We validated this approach with ordinary commercial synthetic polymers, namely polyolefins, a polyamide, and a polyester, which by themselves exhibit no antibacterial activity. A slide made of high-density polyethylene (HDPE) was selected as the initial target. This polymer, as many other materials, lacks reactive groups suitable for a facile chemical modification. Therefore, we decided to coat it with an ultrathin silica layer by a combustion chemical vapor deposition technique (Schinkinger et al., 2001). To this end, we employed (step #1 in FIG. 4) a pen-like torch containing a compressed mixture of 0.6% tetramethylsilane with 7:3 propane-butane (Pyrosil®). When this mixture burns in the air, tetramethylsilane is oxidized to form 2–5-mn $SiO_2$ particles which cover a surface to which the flame is applied (Tiller et al., 1989). The resulting dense, ~100-nm thick $SiO_2$ layer (Schinkinger et al., 2001; Tiller et al., 1989) chemically resembling glass (polysiloxane) can thereafter be readily chemically modified in a uniform fashion regardless of the nature of the bulk material (Tiller et al., 1989 and 1991).

The visual appearance of the HDPE surface did not change after the $SiO_2$ coating procedure. The degree of crosslinking of such a $SiO_2$ layer is lower than that of glass, and numerous Si—OH groups are formed on hydration by water adsorbed from the environment after the deposition process (Schinkinger et al., 2001). Because of these Si—OH groups, the coated HDPE surface is expected to be hydrophilic, in contrast to the very hydrophobic unmodified polymer. To quantify this difference, we measured the contact angle formed by an aqueous drop on a surface, a common method of determining the water affinity of materials (David, 1966). To this end, 0.1 mL of distilled water was placed on the HDPE surface. The angle between the core of the resultant water drop and the surface under it was estimated to be some 120°, indicative of a hydrophobic material. When the same amount of distilled water was placed onto the $SiO_2$-coated HDPE, the water spread on the surface and the contact angle was less than 10° reflecting the surface's hydrophilic character. Independently, the presence of the $SiO_2$ layer on the HDPE slide was confirmed by the silicon and oxygen signals detected in the X-ray photoelectron spectrum.

Next, amino groups were introduced into the $SiO_2$-coated HDPE slide surface by reacting it with 3-aminopropyltriethoxysilane (step #2 in FIG. 4), a standard procedure for the amination of glass surfaces (Bisse et al., 1982). The $NH_2$-functionalized HDPE slide was subsequently alkylated with 1,4-dibromobutane to introduce bromoalkyl groups (step #3 in FIG. 4), which were then reacted with PVP in the presence of 1-bromohexane (step #4 in FIG. 4). Under the conditions used, only a few (out of approximately 1,500) pyridine groups of the PVP chain are alkylated by the surface-bound bromoalkyls, with the majority being alkylated by 1-bromohexane (Tiller et al., 2001). The number of the pyridinium groups on the resultant hexyl-PVP-derivatized HDPE slides, titrated spectrophotometrically with fluorescein, was determined to be 8.2±1.9 nmol/$cm^2$, which is similar to that observed for hexyl-PVP-modified $NH_2$-glass (Tiller et al., 2001).

The generality of the foregoing nanocoating/derivatization approach was confirmed by modifying two other industrial polyolefins, low-density polyethylene (LDPE) and polypropylene (PP), as well as the polyamide nylon and the polyester poly(ethylene terephthalate) (PET). All these synthetic polymers were successfully derivatized as shown in FIG. 4 and exhibited surface densities of the pyridinium groups similar to that of HDPE -8.5±1.8 (LDPE), 7.2±2.1 (PP), 8.0±1.1 (nylon), and 7.5±0.9 (PET) nmol/$cm^2$. All hexyl-PVP-derivatized slides, starting with HDPE, were subsequently examined with respect to their ability to kill airborne bacteria on contact.

To simulate natural deposition of airborne bacteria, as well as contact deposition of bacteria, a suspension in distilled water of the ubiquitous pathogen Gram-positive bacterium *Staphylococcus aureus* (Xiong et al., 2000) was sprayed onto a slide surface and the latter was allowed to dry. The slide was then incubated under nutrient agar overnight as described earlier (Tiller et al., 2001), and the number of viable bacterial cells was determined by colony count. As seen in FIG. 5*a*, left, numerous readily distinguishable bacterial colonies grew on the unmodified HDPE slide. The number of colonies grown on the $SiO_2$-coated or $NH_2$-functionalized HDPE slides (FIG. 4) was essentially the same indicating that these modifications are not toxic to *S. aureus*. In striking contrast, when sprayed onto a hexyl- PVP-modified HDPE slide, 96±3% of the deposited bacterial cells died, i.e., became non-viable (FIG. 5*a*, right, and Table I).

TABLE I

The ability of various commercial synthetic polymers derivatized by hexyl-PVP to kill airborne bacteria on contact.

| | | Percentage of bacteria killed | | | | |
|---|---|---|---|---|---|---|
| Bacterium | Type | HDPE | LDPE | PP | nylon | PET |
| *S. aureus* | Gram (+) | 96 ± 3 | 97 ± 1 | 90 ± 3 | 92 ± 2 | 95 ± 1 |
| *E. coli* | Gram (−) | 97 ± 1 | 96 ± 2 | 98 ± 1 | 98 ± 2 | 95 ± 1 |

Suspensions of bacteria ($10^6$ cells/mL for *S. aureus* and $10^5$ cells/mL for *E. coli*) in distilled water were sprayed on a hexyl-PVP-modified polymer slide, and the latter was air dried for 2 min and incubated under 0.7% agar in a bacterial growth medium overnight; thereafter, the colonies were counted. The number of viable cells obtained in the same manner with the corresponding unmodified polymer slides was used as a standard (i.e., 0% of the bacteria killed). All experiments were performed at least in duplicate, and the errors given indicate the standard deviations.

LDPE, PP, nylon, and PET derivatized with hexyl-PVP were analogously tested for their ability to kill airborne *S. aureus*. As seen in Table I, in all cases the number of bacterial colonies formed plunged 10 to 30-fold compared to those grown on the corresponding unmodified slides.

Next, we tested the killing efficiency of the hexyl-PVP-derivatized surfaces for a representative Gram-negative bacterium, *Escherichia coli*. As seen in FIG. 5*b*, left, many *E. coli* colonies grown on a HDPE slide after spraying, while less dense than those of *S. aureus* grown under the same conditions, are still distinguishable. The surface derivatization with hexyl-PVP slashed their number by 97±3% (FIG. 5*b*, right, and Table I). Inspection of the remaining data in the last line of Table I reveals that the hexyl-PVP modification of LDPE, PP, nylon, and PET slides likewise afforded a 20 to 50-fold drop in the viable *E. coli* cells, following their deposition from the airborne state, when compared to the corresponding unmodified slides.

To test whether the hexyl-PVP chains immobilized using our methodology can leach from the slide surface (and conceivably only then kill the deposited bacteria), modified HDPE slide was placed into a polystyrene Petri dish, and an aqueous suspension of *S. aureus* cells was sprayed on it, as well as on the (non-antibacterial) polystyrene surface. After air drying and incubation under growth agar, only a few (4±2 per $cm^2$) colonies grew on the hexyl-PVP-modified HDPE slide, while a far greater number of colonies (85±5 per $cm^2$) grew on the surface of the surrounding Petri dish, even in the immediate proximity of the slide. The lack of inhibition zones around the hexyl-PVP-slides, characteristic of release of bactericidal agents (Kawabata and Nishiguchi, 1988), indicates that the immobilized polycation does not leach from the slide, i.e., that the airborne bacteria are indeed killed on contact with the slide's surface.

Another important question was whether the hexyl-PVP-derivatized slides can also kill waterborne bacteria. To experimentally simulate a flowing aqueous solution, a polymer slide was placed vertically in a bacterial suspension in PBS, pH 7.0, and the resulting system was gently agitated at 37° C. After a 2-h incubation, the slide was washed with the sterile buffer to remove non-adhered bacteria and then incubated in sterile PBS under the conditions outlined above for 1 h to allow the tentatively adhered bacteria to either detach or adhere irreversibly (Wiencek and Fletcher, 1995). After rinsing the slide with PBS, it was immediately covered with a layer of solid growth agar and incubated overnight at 37° C. This way, all genuinely attached bacterial cells are captured on the slide surface, and those of them still viable can proliferate and form colonies.

As seen in FIG. 6*a*, left, *S. aureus* cells allowed to adhere to an HDPE slide form numerous easily distinguishable colonies. Neither $SiO_2$— nor $NH_2$— modified HDPE slides exhibited an appreciable decline in the number of bacterial colonies grown after the adhesion. However, as seen in FIG. 6*a*, right, the number of *S. aureus* colonies grown on a hexyl-PVP-modified HDPE slide plunged 98±1% (see also Table II).

TABLE II

The ability of hexyl-PVP covalently attached to various commercial polymer slides to kill waterborne bacteria on contact.

| | | Percentage of bacteria killed | | | | |
|---|---|---|---|---|---|---|
| Bacterium | Type | HDPE | LDPE | PP | nylon | PET |
| *S. aureus* | Gram (+) | 98 ± 1 | 99 ± 1 | 97 ± 2 | 97 ± 1 | 99 ± 1 |
| *E. coli* | Gram (−) | 97 ± 2 | 98 ± 2 | n.d. | 99 ± 1 | 98 ± 1 |

Suspensions of bacteria (2 × $10^6$ cells/mL for *S. aureus* and 4 × $10^6$ cells/mL for *E. coli*) in PBS, pH 7.0, was allowed to adhere to the hexyl-PVP-modified polymer surfaces under shaking at 37° C. for 2 h. The slides were rinsed with sterile PBS, pH 7.0, shaken in it at 37° C. for 1 h, rinsed again with it, incubated under 1.5% agar in a bacterial growth medium overnight, and the colonies were counted. N.d. stands for "not determined" because adhered bacterial cells grow but do not form distinguishable colonies on the control slide. For other conditions, see the footnotes to Table I.

It was further demonstrated that hexyl-PVP-derivatized LDPE, PP, nylon, and PET also can kill waterborne bacteria on contact. The data in Table II show that upon the derivatization (FIG. 4) the number of viable adhered *S. aureus* cells drops by 97 to 99% for all polymer slides. Likewise, the modified polymer slides were found to be effective against waterborne *E. coli*. As seen in FIG. 6*b*, left, *E. coli* cells adhered to an unmodified HDPE slide from an aqueous suspension grow a number of distinguishable colonies under the growth agar cover. The colonies on LDPE, nylon, and PET looked similar, while no colonies were distinguishable on PP. Upon the derivatization of HDPE with hexyl-PVP, the number of viable adhered E. coli cells plummeted 97±2% (FIG. 6*b*, right, and Table II). The other modified polymers also displayed drastically lower numbers of adhered viable *E. coli* cells compared to the corresponding unmodified slides, with killing efficiencies of 98–99% observed for LDPE, PET, and nylon (Table II, last line).

Since the experimental conditions for the determination of bactericidal properties of the hexyl-PVP-modified slides against waterborne bacteria were different from those for airborne ones, we again tested for release of the polycation from a slide into the medium. To this end, a hexyl-PVP-modified HDPE slide was incubated for 2 h in sterile PBS with shaking at 37° C., removed, and *S. aureus* cells were added to the remaining solution. The resulting suspension was again shaken at 37° C. for 2 h, and the number of viable bacterial cells was determined by spreading it on growth agar, followed by incubation at 37° C. overnight. The number of bacterial colonies observed, $(42±4)·10^4$ per mL, coincided with that in the control $[(48±7)·\mathbf{10}^4]$. Hence there is no appreciable release of an antibacterial agent from the hexyl-PVP-modified HDPE slide during the bacterial adhesion experiment, and the waterborne bacteria must indeed be killed on contact with the derivatized surface.

Figure 7:
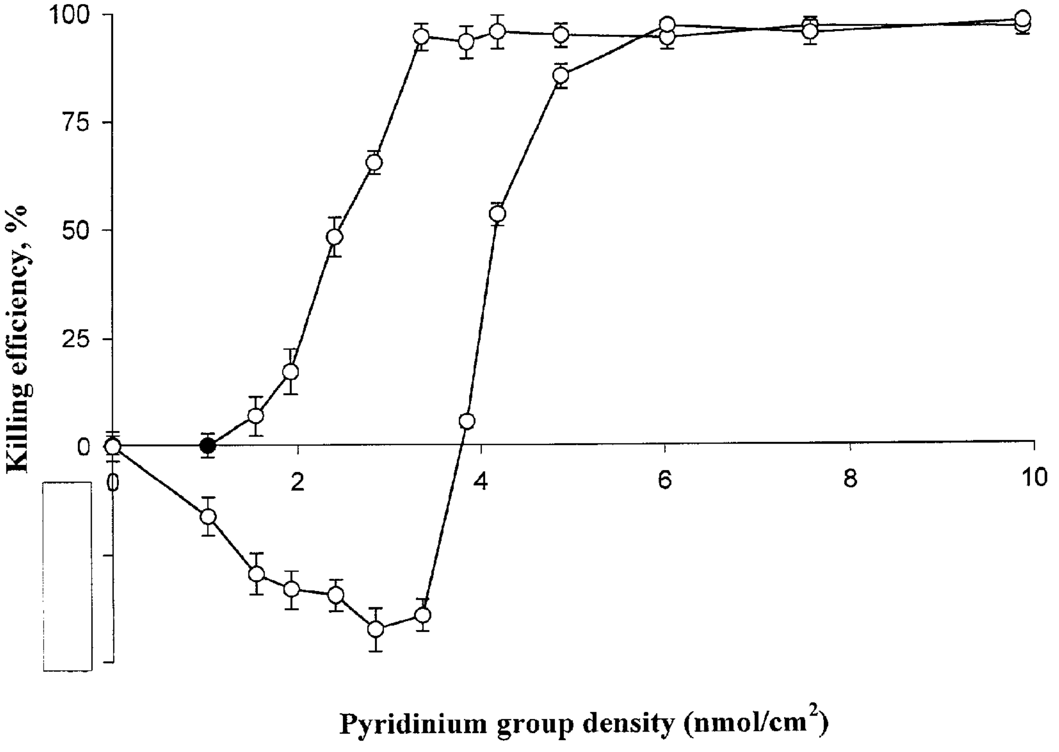
FIG. 7 depicts the killing efficiency of hexyl-PVP-derivatized HDPE toward airborne (●) or waterborne (○) *S. aureus* cells deposited on the modified polymer surface as a function of the surface density of the pyridinium groups. The negative percentages correspond to a greater number of bacterial cells adhered to the modified slides than to the unmodified one.

The bactericidal mechanism of the surface-attached polycationic chains probably involves their penetration into the bacterial membranes, leading to cell damage and death (Tiller et al., 2001). To add a quantitative dimension to this model, HDPE slides were derivatized with hexyl-PVP with varying surface densities of the polycation, and the antibacterial efficiency against airborne or waterborne *S. aureus* cells was measured as outlined above. As seen in FIG. 7, the bactericidal effect is expressed only when the surface density of the pyridinium groups exceeds some 3 nmoles per $cm^2$ for the airborne bacterium and 6 nmoles per $cm^2$ for the waterborne one, with no additional increase thereafter. The difference between the two curves is presumably due to the fact that the sprayed bacterial cells, in contrast to those in solution, have no possibility of detaching from the surface and hence are killed at lower pyridinium group densities. These observations show the critical dependence of the material's ability to kill bacteria on the density of coverage of its surface with the polycation.

In closing, we have developed a general method of derivatizing surfaces with the antibacterial polymer hexyl-PVP applicable to common materials. The hexyl-PVP-modified surfaces of the synthetic polymers HDPE, LDPE, PP, nylon, and PET kill up to 99% of contact-deposited *S. aureus* and *E. coli* cells. The methodology should be useful in rendering numerous products bactericidal both in dry and wet states; the surfaces could be rejuvenated simply by periodic washings.

References Cited

Arnold J W, Bailey G W. 2000. Surface finishes on stainless steel reduce bacterial attachment and early biofilm formation: scanning electron and atomic force microscopy study. Poultry Sci 79:1839–1845.

Bisse E, Scholer A, Vonderschmitt D J. 1982. A new method for coupling glucose dehydrogenase to glass tubes activated with titanium tetrachloride. FEBS Lett 138:316–318.

Costerton J W, Stewart P S, Greenberg E P. 1999. Bacterial biofilms: a common cause of persistent infections. Science 286:1318–1322.

Cunliffe D, Smart C A, Alexander C, Vulfson E N. 1999. Bacterial adhesion at synthetic surfaces. Appl Environ Microbiol 165:4995–5002.

David J. 1966. The idea of water repellency. Text Inst Ind 4:293–295.

Hogt A H, Dankert J, Feijen J. 1986. Adhesion of coagulase-negative staphylococci to methacrylate polymers and copolymers. J Biomed Mater Res 20:533–545.

Kawabata N, Nishiguchi M. 1988. Antibacterial activity of soluble pyridinium-type polymers. Appl Environ Microbiol 54:2532–2535.

Kohnen W, Jansen B. 1995. Polymer materials for the prevention of catheter-related infections. Zbl Bakt 283: 175–186.

Lewis K. 2001. The riddle of biofilm resistance. Antimicrob Agents Chemother 45:999–1007.

Medlin J. 1997. Germ warfare. Environ Health Persp 105:290–292.

Nohr R S, Macdonald G J. 1994. New biomaterials through surface segregation phenomenon: new quaternary ammonium compounds as antibacterial agents. J Biomater Sci, Polymer Edn 5:607–619.

Schinkinger B, Petzold R, Tiller H-J, Grundmeier G. 2001. Chemical structure and morphology of ultrathin combustion CVD layers on zinc coated steel. Appl Surf Sci 179:79–87.

Shearer A E H, Paik J S, Hoover D G, Haynie S L, Kelley M J. 2000. Potential of an antibacterial ultraviolet-irradiated nylon film. Biotechnol Bioeng 67:141–146.

Tiller H J, Goebel R, Gutmann N. 1991. Silicate coupling layer for metal to polymer adhesion improvement. Physical-chemical fundamentals and technological importance. Makromol Chem, Macromol Symp 50:125–135.

Tiller H J, Goebel R, Magnus B, Garschke A, Musil R. 1989. A new concept of metal-resin adhesion using an intermediate layer of silicon oxide ($SiO_x$)-carbon. Thin Solid Films 169:159–168.

Tiller H J, Kaiser W D, Kleinert H, Goebel R. 1989. The Silicoater method improves bond strength and resistance to aging. Adhaesion 33:27–31.

Tiller J C, Liao C-J, Lewis K, Klibanov A M. 2001. Designing surfaces that kill bacteria on contact. Proc Natl Acad Sci USA 98:5981–5985.

Wiencek K M, Fletcher M. 1995. Bacterial adhesion to hydroxyl- and methyl-terminated alkanethiol self-assembled monolayers. J Bacteriol 177:1959–1966.

Xiong Y, Yeaman M R, Bayer A S. 2000. Linezolid: A new antibiotic. Drugs Today 36:529–539.

Example 13

Insights into Bactericidal Action of Surface-Attached Poly (vinyl-N-hexylpyridinium) Chains The surface of polyethylene slides nanocoated with silica and derivatized with long-chain poly(vinyl-N-hexylpyridinium) becomes permanently bactericidal: it kills 90–99% of (both airborne and waterborne) wild-type and antibiotic-resistant strains of the human pathogen *Staphylococcus aureus*. The material created was similarly lethal to strains expressing multidrug resistance pumps, the only known mechanism of resistance to cationic antiseptics.

Creating inherently bactericidal materials that could be used to make common objects would be a major step toward a healthier living. Recently, we (Tiller et al. 2001 and 2002) have discovered that when certain long-chain, hydrophobic polycations are immobilized onto surfaces of glass or plastics, the latter acquire the ability to efficiently kill bacteria on contact. Specifically, various surfaces covalently coated with poly(vinyl-N-hexylpyridinium) (hexyl-PVP) have been found to kill the vast majority of bacteria, both Gram-positive and Gram-negative, either deposited onto them through aerosols (followed by drying) or allowed to attach from aqueous solution.

In the present study, we have further explored this potentially useful phenomenon. In particular, it has been ascertained that polyethylene surface-derivatized with hexyl-PVP is equally lethal against wild-type and mutant, including antibiotic-resistant, strains of the ubiquitous pathogenic bacterium *Staphylococcus aureus*. The dead cells can be readily removed—and the surface fully rejuvenated—by washing with a detergent. *S. aureus* cells collected during the logarithmic growth phase are as susceptible to the bactericidal action as those in the stationary phase.

Materials

The list of *S. aureus* strains used in this study is given in Table 1. A hand-held burner containing 0.6% (v/v) tetramethylsilane in a propane/butane mixture (7:3, v/v) (Pyrosil®) was from SurA Instruments GmbH (Jena, Germany). High-density polyethylene sheets were purchased from Polymer Plastic Co. Poly(4-vinylpyridine) (PVP) (Mw 160,000 g/mol), 3-aminopropyltriethoxysilane, 1,4-dibromobutane, 1-bromohexane, and all other chemicals and solvents were obtained from Aldrich Chemical Co. and used without further purification.

TABLE 1

| Strains of *Staphylococcus aureus* used in this study. | | |
|---|---|---|
| Strain | Description | Reference |
| 8325-4 | Wild-type parent of 1758 | Kaatz et al. 1999 |
| 1758 | norA | Kaatz et al. 1999 |
| 982 | Wild-type parent of 2355 | Rouch et al. 1990 |
| 2355 | QacA$^+$, Kan$^r$ | Rouch et al. 1990 |
| ATCC 700698 | Methicillin-resistant strain | Hiramatsu 1997 |
| ATCC BAA-38 | Methicillin-resistant strain | De Lencastre 2000 |
| ATCC BAA-39 | Methicillin-resistant strain | De Lencastre 1997 |
| ATCC 33807 | No pyrogenic exotoxin C | [a] |

[a]Obtained from ATCC.

Surface Modification

A polyethylene slide (7.5×2.5 cm) was ultrasonicated in isopropyl alcohol for 5 min and dried at 80° C. The front (oxidizing) part of the flame of a hand-held burner was fanned over the slide surface for 15 s, and the slide was stored under air overnight. The $SiO_2$-coated slide was aminated with a 20% solution of 3-aminopropyltriethoxysilane in dry toluene at room temperature for 3 h. The aminated slide was immersed in a solution containing 9 mL of 1,4-dibromobutane, 90 mL of dry nitromethane, and 0.1 mL of triethylamine with stirring at 60° C. for 5 h, followed by placing in a freshly prepared solution of 9 g of PVP, 10 mL of 1-bromohexane, and 81 mL of nitromethane. After stirring at 75° C. for 9 h, the slide was thoroughly rinsed with methanol and distilled water, and dried under air.

Antibacterial Efficiency Determination

Bacteria were grown in yeast-dextrose broth (Cunliffe et al. 1999) at 37° C. with aeration at 200 rpm for 6–8 hours. The inoculum from an overnight culture was transferred into 0.1 M PBS (approximately $10^{11}$ cells/mL) and then introduced into the growth medium at a 1:500 dilution.

The airborne bacterial suspension was prepared as described earlier (Tiller et al. 2001). The bacterial cells were centrifuged at 5,160×g for 10 min and washed with distilled water twice. A bacterial suspension at a concentration of 106 cells/mL in distilled water was sprayed at a rate of approximate 10 mL/min onto the surface of a slide in a fume hood. After drying for 2 min under air, the slide was placed in a Petri dish, and growth agar (0.7% agar in the yeast-dextrose broth, autoclaved, and cooled to 37° C.) was added. The Petri dish was sealed and incubated at 37° C. overnight. The grown bacterial colonies were counted on a light box.

The waterborne bacterial suspension was prepared as follows: bacterial cells were centrifuged at 5,160×g for 10 min, washed twice with PBS at pH 7.0, re-suspended in the same buffer, and diluted to $2\times10^6$ cells/mL. A slide was immersed in 45 mL of the suspension and incubated with shaking at 200 rpm at 37° C. for 2 h, then rinsed three times with sterile PBS, and incubated in it for 1 h. The slide was immediately covered with a layer of solid growth agar (1.5% agar in the yeast-dextrose broth, autoclaved, poured into a Petri dish, and dried under reduced pressure at room temperature overnight). The bacterial colonies were then counted.

Synthesis of Pyridinium-Containing Monomer and Polymer

Pyridine (10 mL), hexyl bromide (18 mL), and triethylamine (0.1 mL) were dissolved in 122 mL of toluene, and the solution was stirred at 75° C. for 9 h. The solvent was then removed under reduced pressure. N-Hexylpyridinium bromide thus obtained was washed with hexane four times and dried overnight under vacuum.

Poly(4-vinylpyridine) (5.25 g), methyl iodide (13 mL), and triethylamine (0.1 mL) were dissolved in 87 mL of nitromethane, and the solution was stirred at 75° C. for 9 h. After cooling to room temperature, the solvent was removed and 100 mL of toluene was added to the residue. Poly(4-vinyl-N-methylpyridinium iodide), insoluble in toluene, was recovered by filtration, washed with toluene and acetone, and dried.

Results & Discussion

We have answered certain questions concerning the mechanism and practicalities of the bactericidal effect of surfaces derivatized with poly(vinyl-N-alkylpyridinium) chains (Tiller et al. 2001 and 2002). For example, 7.5×2.5 cm slides cut out of a large sheet of commercial high-density polyethylene were coated with a nanolayer of silica, followed by the covalent attachment of 160,000-g/mol hexyl-PVP, as previously described (Tiller et al. 2002). The antibacterial activity of the resultant slides was tested against the common pathogen *S. aureus* in two distinct modalities (referred to as "airborne" and "waterborne"). In the airborne case, an aqueous suspension of the bacterial cells was sprayed onto a slide, followed by drying, overlaying with growth agar, incubation at 37° C., and counting the number of bacterial colonies. In the waterborne case, a slide was immersed in an aqueous suspension of the bacterial cells, incubated there at 37° C., washed, covered with solid growth agar, and incubated at 37° C. again, followed by counting the number of bacterial colonies.

When wild-type *S. aureus* cells were deposited onto the surface of an unmodified high-density polyethylene slide via the airborne method, followed by cultivation as described above, 308±16 colonies were subsequently detected in a 3.75 $cm^2$ frontal area. The same experiment was performed with the slide coated with silica and with that also aminated; the corresponding numbers of bacterial colonies were 339±2 and 228±2, respectively. Thus the bacterial cells deposited onto all three different surfaces remain highly viable. In contrast, when the identical procedure was applied to the hexyl-PVP-derivatized slide, merely 14+1 bacterial colonies were observed in a 3.75-$cm^2$ frontal area, i.e., 5±1% compared to the unmodified slide. Likewise, with waterborne *S. aureus* cells, only 4±2% of colonies were counted on the immobilized hexyl-PVP surface compared to the original polyethylene slide. These 95% + killing efficiencies are analogous to those discovered previously (Tiller et al. 2001 and 2002) for surfaces modified with hexyl-PVP.

Next, we addressed the question of the durability of the aforementioned hexyl-PVP surface protection. To this end, after the colonies grown from the surviving *S. aureus* cells were counted, they were removed by thoroughly washing the hexyl-PVP-derivatized slides with 0.1 M cetyltrimethylammonium chloride in water, followed by rinsing with distilled water. The resultant washed slides were re-used for the deposition of either airborne or waterborne *S. aureus*. The percentages of the colonies formed, as compared to those on the identically washed unmodified polyethylene slides, were 4±1% and 2±1%, respectively. Thus washing with the detergent has no effect on the bactericidal potency of immobilized hexyl-PVP.

In our studies thus far, both herein and elsewhere (Tiller et al. 2001 and 2002), bacterial cells used in all experiments were in the stationary phase of their growth curve. It was of interest to establish whether the cells in the logarithmic phase of growth would be equally susceptible to the antibacterial action of the surface-attached hexyl-PVP chains. Consequently, we carried out a fermentation of *S. aureus* whereby the cell concentration was monitored as a function of time. The resultant data yielded a classical sigmoidal curve (Ingraham et al. 1983), with the stationary phase fully reached after 6 h under our conditions (see Methods). Instead of collecting the bacterial cells after 6–8 h as before, we did so after just 4 h, i.e., during their logarithmic growth phase. When these cells, airborne or waterborne, were deposited onto hexyl-PVP-derivatized slides, the killing efficiencies obtained (compared to the same cells on the unmodified polyethylene slides) were 5±2% and 2±1%, respectively, i.e., identical to the values observed for the cells in their stationary phase (see above).

Figure 8:
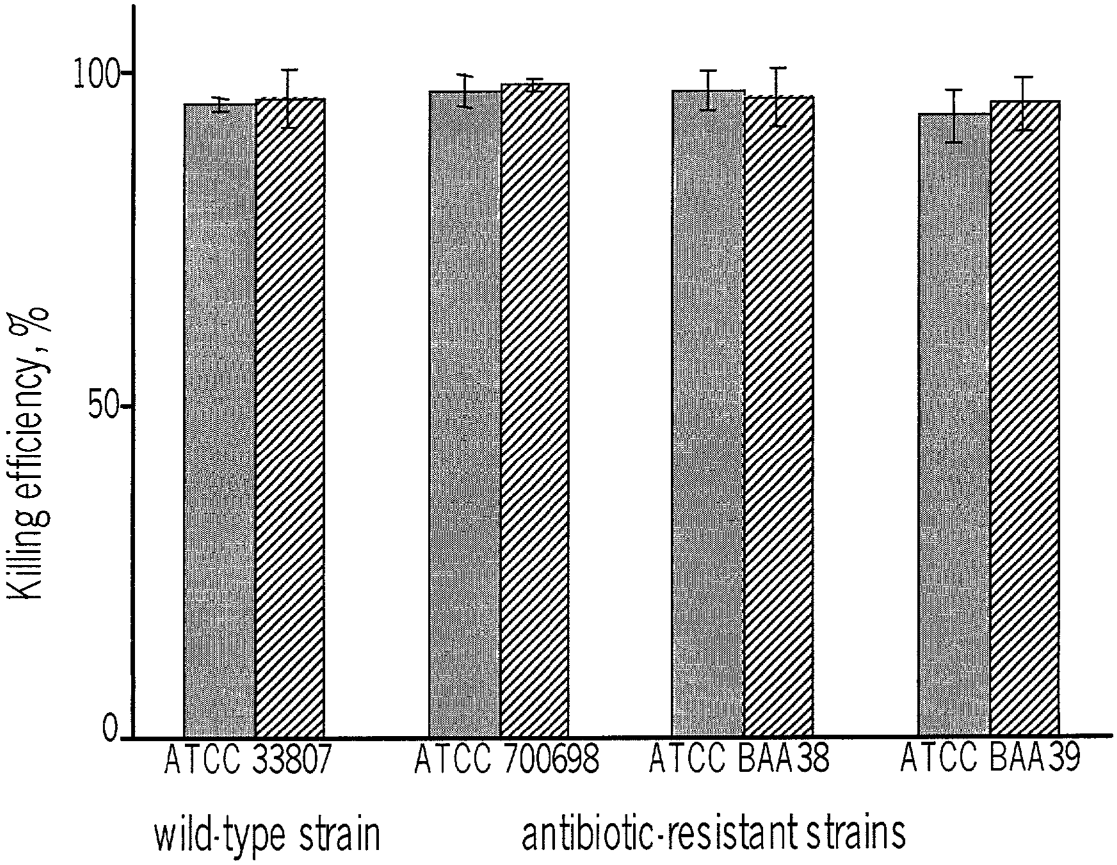
FIG. 8 depicts graphically the bactericidal activity of polyethylene slides covalently coated with hexyl-PVP against wild-type and various antibiotic-resistant strains of *S. aureus*. Either airborne (shaded bars) or waterborne (dashed bars) bacterial suspensions were deposited onto the slide surface. The standard deviations from the mean killing efficiency values are represented by error bars.

Multidrug resistant (MDR) bacterial strains pose a major threat to human health (Levy 1998, Lewis et al. 2001). With this in mind, we tested whether immobilized hexyl-PVP would be effective against such strains. Toward this end, in addition to the heretofore used wild strain of *S. aureus* (ATCC 33807), we explored three different antibiotic-resistant strains (Kluytmans et al. 1997)—ATCC 700698 (resistant to methicillin), ATCC BAA-38 (resistant to methicillin, penicillin, streptomycin, and tetracycline), and ATCC BAA-39 (resistant to penicillin, tetracycline, imipenem, cefaclor, oxacillin, tobramycin, cephalexin, cefuroxime, gentamicins, amoxicillin, clindamycin, erythromycin, and cephamandole). As seen in FIG. 8, polyethylene slides coated with hexyl-PVP were similarly lethal to these bacterial strains, whether airborne or waterborne—the killing efficiencies in all instances well exceeded 90%. Iimmobilized hexyl-PVP chains likely exert their bactericidal effect by penetrating the bacterial cell wall/membrane and perhaps causing autolysis (Tiller et al 2001).

Figure 9:
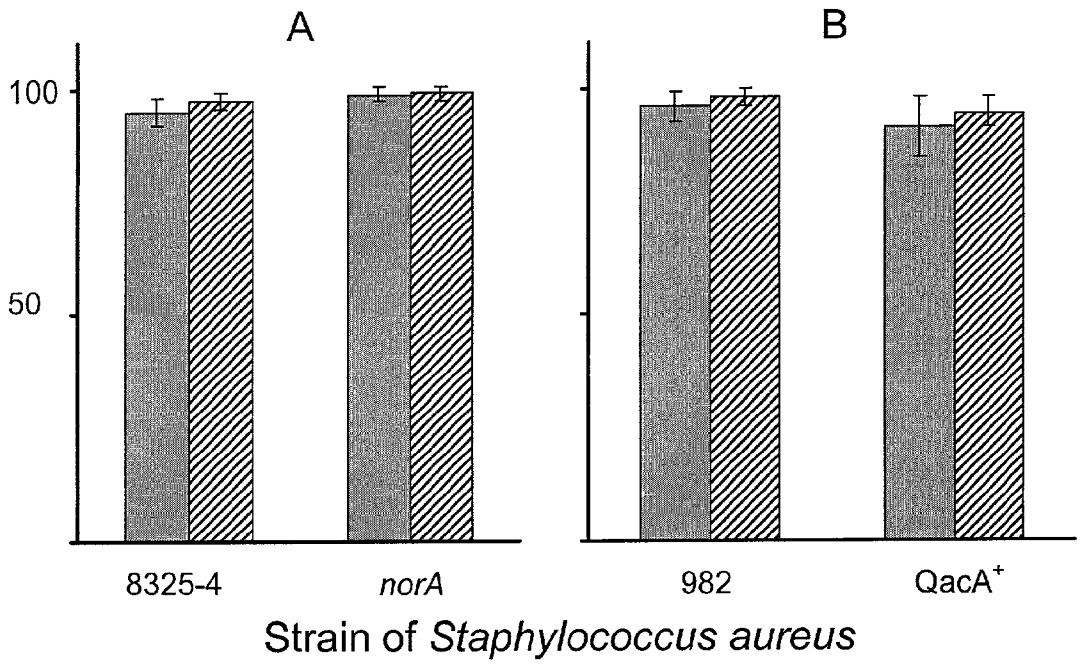
FIG. 9 depicts graphically the bactericidal activity of polyethylene slides covalently coated with hexyl-PVP against two parent/mutant pairs of *S. aureus* strains. In the first pair (A), the mutant is missing the MDR pump encoded by the norA gene (which had been knocked out), while its otherwise identical parent has it. In the second pair (B), the parent lacks the MDR pump encoded by the qacA gene, whereas the plasmid-bearing strain has it.

Like all other bacteria studied (Lewis 1994, Lewis et al. 2001), *S. aureus* possesses several MDR pumps that expel various toxic compounds from the cell. For example, the NorA MDR pump protects the cells from numerous amphipathic cations including the common disinfectant benzalkonium chloride (Ng et al. 1994). Consequently, the mutant of *S. aureus* with a knockout in the norA gene coding for the MDR pump has a substantially greater sensitivity to such compounds (Hsieh et al. 1998). Since hexyl-PVP, like benzalkonium, is a hydrophobic quaternary ammonium cation, we decided to test the sensitivity of the norA mutant strain to immobilized hexyl-PVP. The results of this experiment are depicted in FIG. 9A. One can see that the killing efficiencies against the pump-lacking mutant were somewhat higher than of its pump-competent parent—99±1% for both airborne and waterborne cells vs. 95±2% and 97±1%, respectively.

We carried out similar experiments with a *S. aureus* strain with an additional MDR pump (denoted $QacA^+$) expressed from a natural transmissible plasmid compared to its parent. This strain had a slightly higher resistance to immobilized hexyl-PVP than its pump-deficient parent (FIG. 2B)—92±3% and 94±3% for the airborne and waterborne mutant, respectively, vs. 96±2% and 98±1% for its parent.

The very small difference in observed susceptibilities to hexyl-PVP between strains lacking/overexpressing MDRs suggest that the polymeric form of the antiseptic is not effectively extruded by the pump. Alternatively, N-hexylpyridinium may not be a substrate for MDRs. In order to distinguish between these possibilities, cells were treated with an aqueous solution of N-hexylpyridinium bromide, and the minimal inhibitory concentration (MIC) was determined. That compound turned out to be a very weak antimicrobial, with an MIC of 4 mg/mL against wild-type *S. aureus* (Table 2). This value is more than 1,000 times above that of the conventional antiseptic benzalkonium chloride (Table 2). There was a difference in strain susceptibilities to N-hexylpyridinium depending on their MDR status. Thus the MIC of the norA strain was 0.5 mg/mL, and that of the $QacA^+$ strain was above 4 mg/mL. This qualitatively resembles the difference in susceptibilities of these strains to benzalkonium chloride and shows that while N-hexyl-pyridinium is a weak antimicrobial, it is a reasonable substrate for MDRs. When water-soluble poly(vinyl-N-methylpyridinium iodide) was tested instead (note that hexyl-PVP itself, used in its immobilized form in our studies thus far, is not soluble in water and therefore could not be used in MIC studies), the MIC value was found to be 75 μg/mL, i.e., considerably lower than that of the monomeric precursor N-hexylpyridinium bromide. There was no difference in the MIC values of this compound among the strains tested. It thus appears that polymerization of an antiseptic has two consequences for its properties—increases its potency and makes it insensitive to the action of MDR pumps.

TABLE 2

The minimal inhibitory concentration (MIC) for quatenary ammonium containing monomers and polymer.

| | Benzalkonium chloride MIC (μg/mL) | N-Hexylpyridinium Bromide MIC (μg/mL) | Poly(vinyl-N-methyl-pyridinium iodide) MIC (μg/mL) |
|---|---|---|---|
| ATCC 33807 | 2.5 | 4,000 | 75 |
| ATCC 700698 | 2.5 | >4,000 | 75 |
| ATCC BAA-38 | 2.5 | >4,000 | 75 |
| ATCC BAA-39 | 2.5 | 4,000 | 75 |
| 8325-4 | 2.5 | 4,000 | 75 |
| norA | 0.6 | 500 | 75 |
| 982 | 2.5 | 4,000 | 75 |
| $QacA^+$ | 5.0 | >4,000 | 75 |

Development of a resistance is a major concern in introducing any new antimicrobial. Extrusion by MDRs is the only known mechanism of resistance to hydrophobic cationic antiseptics (Lewis 2001, Severina et al. 2002). Our findings suggest that resistance to surface-attached hexyl-PVP is unlikely to develop through this mechanism.

References Cited

Cunliffe D, Smart C A, Alexander C, Vulfson E N (1999) Bacterial adhesion at synthetic surfaces. *Appl. Environ. Microbiol.* 65: 4995–5002.

De Lencastre H (2000) Archaic strains of methicillin-resistant *Staphylococcus aureus*: molecular and microbiological properties of isolates from 1960s in Denmark. *Microb. Drug Resist.* 6: 1–10.

Hiramatsu K (1997) Dissemination in Japanese hospitals of strains of *Staphylococcus aureus* heterogeneously resistant to vancomycin. *Lancet* 350: 1670–1673.

Hsieh P, Siegel S A, Rogers B, Davis D, Lewis K (1998) Bacteria lacking a multidrug pump: a sensitive tool for drug discovery. *Proc. Natl. Acad. Sci. USA* 95: 6602–6606.

Ingraham J L, Maaløe O, Neidhardt F C (1983) *Growth of the Bacterial Cell,* Chapter 5. Sunderland (Mass.): Sinaner.

Kaatz G W, Seo S M, Foste T J (1999) Introduction of a norA promoter region mutation into the chromosome of a fluoroquinolone-susceptible strain of *Staphylococcus aureus* using plasmid integration. *Antimicrob. Agents Chemother.* 43: 2222–2224.

Kluytmans J, van Belkum A, Verbrugh H (1997) Nasal carriage of *Staphylococcus aureus*: epidemology, underlying mechanisms, and associated risks. *Clin. Microbiol. Rev.* 10: 505–520.

Levy S B (1998) The challenge of antibiotic resistance. *Science* 278:46–53.

Lewis K (2001) In search of natural substrates and inhibitors of MDR pumps. *J. Mol. Microbiol. Biotechnol.* 3: 247–254.

Lewis K, Lomovskaya O (2001) Drug efflux. In *Bacterial Resistance to Antimicrobials: Mechanisms, Genetics, Medical Practice and Public Health.* Lewis K, Salyers A, Taber H, Wax R, eds. (2001) New York: Marcel Dekker.

Lewis K (1994) Multidrug resistance pumps in bacteria: variations on a theme. *Trends Biochem. Sci.* 19: 119–123.

Lewis K, Salyers A, Taber H, Wax R, eds. (2001) *Bacterial Resistance to Antimicrobials: Mechanisms, Genetics, Medical Practice and Public Health.* New York: Marcel Dekker.

Ng E Y, Trucksis M, Hooper D C (1994) Quinolone resistance mediated by norA: physiologic characterization and relationship to flqB, a quinolone resistance locus on the *Staphylococcus aureus* chromosome. *Antimicrob. Agents Chemother.* 38: 1345–1355.

Rouch D A, Cram D S, DiBerardino D, Littlejohn T G, Skurray R A (1990) Efflux-mediated antiseptic resistance gene qacA from *Staphylococcus aureus*: common ancestry with tetracycline- and sugar-transport proteins. *Mol. Microbiol.* 4: 2051–2062.

Severina II, Muntyan M S, Lewis K, Skulachev V P (2002) Transfer of cationic antibacterial agents berberine, palmatine and benzalkonium through bimolecular planar phospholipid film and *Staphylococcus aureus* membrane. *Biochem. Internat.* in press.

Tiller J C, Lee S B, Lewis K, Klibanov A M (2002) Polymer surfaces derivatized with poly(vinyl-N-hexylpyridinium) kill both air- and water-borne bacteria. *Biotechnol. Bioeng.* 79: in press.

Tiller J C, Liao C-J, Lewis K, Klibanov A M (2001) Designing surfaces that kill bacteria on contact. *Proc. Natl. Acad. Sci. USA* 98: 5981–5985.

Incorporation by Reference

All publications and patents mentioned herein, are hereby incorporated by reference in their entirety as if each individual publication or patent was specifically and individually indicated to be incorporated by reference. In case of conflict, the present application, including any definitions herein, will control.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A composition comprising a material and a compound immobilized to the surface of the material by a covalent bond, wherein the surface comprises silicon oxide and the immobilized compound is a water-soluble lipophilic polycation polymer comprising poly(N-alkylvinylpyridinium halide).

2. A composition comprising a surface and a compound covalently bonded to the surface, wherein the surface comprises silicon oxide and the compound is represented by formula I:

I

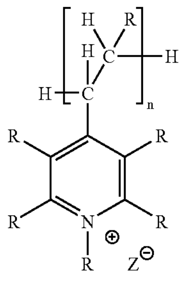

wherein

R represents individually for each occurrence hydrogen, alkyl, alkenyl, alkynyl, acyl, aryl, carboxylate, alkoxycarbonyl, aryloxycarbonyl, carboxamido, alkylamino, acylamino, alkoxyl, acyloxy, hydroxyalkyl, alkoxyalkyl, aminoalkyl, (alkylamino)alkyl, alkylthio, thioalkyl, or (alkylthio)alkyl;

R' represents independently for each occurrence alkyl or a tether to the surface represented by formula 1*a:*

1a

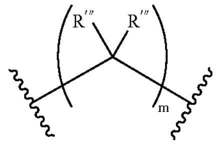

wherein, R''' is H or alkyl; and m is 1–30;

Z represents independently for each occurrence Cl, Br, or I; and n is an integer between about 31 and 1500.

3. The composition of claim 2 wherein the tether is represented by Formula 1*a:*

1a

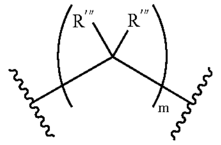

wherein, R''' is H; and m is 1–30.

4. The composition of claim 3 wherein the tether is a —$C_4H_8$—group.

5. The composition of claim 2, wherein the compound covalently bonded to the surface has a weight average molecule weight of at least 60,000 g/mol.

6. The composition of claim 2, wherein the compound covalently bonded to the surface has a weight average molecule weight in the range of 150,000 g/mol.

7. The composition of claim 2, wherein the compound covalently bonded to the surface is poly(4-vinyl-N-alkylpyridinium bromide).

8. The composition of claim 6, wherein the compound covalently bonded to the surface is poly(4-vinyl-N-hexylpyridinium bromide).

9. The composition of claim 2 wherein the surface further comprises low density polyethylene (LDPE), high density polyethylene (HDPE), polypropylene (PP), or poly(ethylene terephthalate) (PET).

10. The composition of claim 2, wherein the surface is the surface of a medical device.

11. The composition of claim 10, wherein the medical device is selected from the group consisting of pins, screws, plates, ventriculoatrial shunts, ventriculoperitoneal shunts, dialysis shunts, heart valves, pacemakers, infusion pumps, vascular grafting prostheses, stents, sutures, surgical meshes, replacement prostheses, breast implants, tissue expanders, contact lenses, stoma appliances, artificial larynx, endotracheal tubes, tracheal tubes, gastrostomy tubes, biliary drainage tubes, biliary steals, catheters, bandages, adhesive tapes, and clear plastic adherent sheets.

12. A composition comprising a surface and a compound covalently bonded to the surface, wherein the surface comprises silicon oxide and the compound is represented by formula I:

I

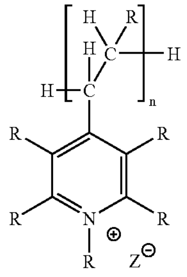

wherein

R represents individually for each occurrence hydrogen, alkyl, alkenyl, alkynyl, acyl, aryl, carboxylate, alkoxycarbonyl, aryloxycarbonyl, carboxamido, alkylamino, acylamino, alkoxyl, acyloxy, hydroxyalkyl, alkoxyalkyl, aminoalkyl, (alkylamino)alkyl, alkylthio, thioalkyl, (alkylthio)alkyl, carbamoyl, or a tether to the surface having Formula 1*b*:

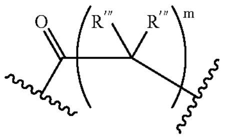

R' represents individually for each occurrence alkyl, alkenyl, alkynyl, acyl, or aryl;

Z represents independently for each occurrence Cl, Br) or I; and n is an integer between about 31 and about 1500.

13. The composition of claim 12, wherein R' is alkyl.

14. The composition of claim 12, wherein the compound covalently bonded to the surface has a weight average molecule weight of at least 60,000 g/mol.

15. The composition of claim 12, wherein the compound covalently bonded to the surface has a weight average molecule weight in the range of 150,000 g/mol.

16. The composition of claim 12, wherein the compound covalently bonded to the surface is poly(4-vinyl-N-alkylpyridinium bromide).

17. The composition of claim 12, wherein the compound covalently bonded to the surface is poly(4-vinyl-N-hexylpyridinium bromide).

18. The composition of claim 12 wherein the surface further comprises low density polyethylene (LDPE), high density polyethylene (HDPB), polypropylene (PP), or poly (ethylene terephthalate) (PET).

19. The composition of claim 12, wherein the surface is the surface of a medical device.

20. The composition of claim 19, wherein the medical device is selected from the group consisting of pins, screws, plates, ventriculoatrial shunts, ventriculoperitoneal shunts, dialysis shunts, heart valves, pacemakers, infusion pumps, vascular grafting prostheses, stents, sutures, surgical meshes, replacement prostheses, breast implants, tissue expanders, contact lenses, stoma appliances, artificial larynx, endotracheal tubes, tracheal tubes, gastrostomy tubes, biliary drainage tubes, biliary stents, catheters, bandages, adhesive tapes, and clear plastic adherent sheets.

* * * * *

UNITED STATES PATENT AND TRADEMARK OFFICE

CERTIFICATE OF CORRECTION

PATENT NO. : 7,151,139 B2
APPLICATION NO. : 10/123860
DATED : December 19, 2006
INVENTOR(S) : Joerg C. Tiller et al.

It is certified that error appears in the above-identified patent and that said Letters Patent is hereby corrected as shown below:

Claim 2, column 50, lines 1-15, replace formula I with

--

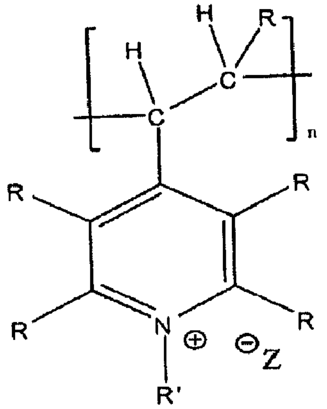

--.

Claim 11, column 51, line 17, replace “steals” with --stents--.
Claim 12, column 51, lines 27-38, the N-linked group in formula 1 should be --R'--.
Claim 12, column 52, line 10, insert --wherein, R'” is H or alkyl; and m is 1-4;-- before “R' represents”.
Claim 12, column 52, line 12, replace “Br)” with --Br,--.
Claim 18, column 52, line 31, replace “HDPB” with --HDPE--.

Signed and Sealed this

Twenty-third Day of September, 2008

JON W. DUDAS
*Director of the United States Patent and Trademark Office*